United States Patent [19]

Immer et al.

[11] 4,081,530
[45] Mar. 28, 1978

[54] EXTENDED CHAIN DERIVATIVES OF SOMATOSTATIN

[75] Inventors: Hans U. Immer, Mt. Royal; Verner R. Nelson, Kirkland; Kazimir Sestanj, Pointe Claire, all of Canada

[73] Assignee: Ayerst, McKenna & Harrison Limited, Montreal, Canada

[21] Appl. No.: 583,947

[22] Filed: Jun. 4, 1975

[51] Int. Cl.$^2$ .................. A61K 37/00; C07C 103/52
[52] U.S. Cl. .......................... 424/177; 260/112.5 S
[58] Field of Search ................ 260/112.5 S; 424/177

[56] References Cited

U.S. PATENT DOCUMENTS

| 3,904,594 | 9/1975 | Guillemin et al. | 260/112.5 S |
| 3,917,578 | 11/1975 | Immer et al. | 260/112.5 S |
| 3,917,581 | 11/1975 | Immer et al. | 260/112.5 S |
| 3,931,140 | 1/1976 | Sarantakis | 260/112.5 S |

Primary Examiner—Delbert R. Phillips

Attorney, Agent, or Firm—Stephen Venetianer

[57] ABSTRACT

Compounds of the formula 1 or 1$a$ $R^1$-Gly-Gly-Ala-Gly- (I)

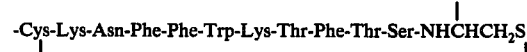

$R^1$-Gly-Gly-Ala-Gly- (Ia)

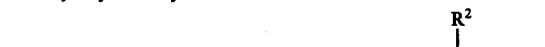

wherein $R^1$ is H—, H—Gly or H—Leu and $R^2$ is H or COOH and pharmaceutically acceptable salts thereof, are disclosed. The compounds of formulae 1 and 1$a$ are useful for the management of diabetes and the treatment of acromegaly. Methods for their use are also disclosed.

27 Claims, No Drawings

EXTENDED CHAIN DERIVATIVES OF SOMATOSTATIN

BACKGROUND OF THIS INVENTION a. Field of Invention

This invention relates to derivatives of the tetradecapeptide somatostatin. More particularly, this invention concerns extended chain derivatives and salts thereof, a process for preparing the derivatives and salts, intermediates used in the process and methods for using the extended chain derivatives and their salts.

b. Prior Art

The name "somatostatin" has been proposed for the factor found in hypothalamic extracts which inhibits the secretion of growth hormone (siomatotropin). The structure of this factor has been elucidated by P. Brazeau, et al., Science, 179, 77 (1973) and reported to be the following tetradecapeptide structure:

The abbreviations used herein for the various amino acids are Ala, alanine; Asn, asparagine; Cys, cysteine; Gly, glycine; Lys, lysine; Phe, phenylalanine; Ser, serine; Thr, threonine; and Trp, tryptophane.

The constitution of the tetradecapeptide somatostatin has been confirmed by synthesis; for example, see D. Sarantakis and W. A. McKinley, Biochem. Biophys. Res. Comm., 54 234 (1973) and J. Rivier, et al., Compt. Rend. Ser. D, 276, 2737 (1973).

The important physiological activity of this tetradecapeptide established it as a compound of significance for clinical pharmacology relating to the treatment of acromegaly and the management of juvenile diabetes; for example, see K. Lundbaek, et al., Lancet, 2, 131 (1970) and R. Guillemin in "Chemistry and Biology of Peptides," J. Meienhofer, Ed., 3rd American Peptide Symposium Boston 1972, Ann Arbor Science Publications, Ann Arbor, Mich., 1972.

The linear form of somatostatin, having two sulfhydryl groups instead of a disulfide bridge, has been prepared recently by J. E. F. Rivier, J. Amer. Chem. Soc., 96, 2986 (1974). He reports that the linear form is equipotent to somatostatin based on the ability of the two compounds to inhibit the rate of secretion of growth hormone by rat pituitary cells in monolayer tissue cultures.

Only recently have there been reported polypeptides, other than the natural hormone and its linear form, having somatostatin-like activity. D. Sarantakis, et al., Biochem. Biophys. Res. Comm., 55, 538 (1973) recently reported the synthesis of the somatostatin analog, [Ala³,¹⁴]-somatostatin, by solid phase methods. This analog exhibited a very small amount of activity, about 0.01% of somatostatin's potency. P. Brazeau, et al., Biochem. Biophys. Res. Comm., 60, 1202 (1974) recently reported the synthesis of a number of acylated des-[Ala¹-Gly²]-somatostatin compounds, by solid phase methods.

The present invention discloses extended chain derivatives of somatostatin which show enhanced activity of the natural hormone and a long duration of activity.

The derivatives are prepared readily by a convenient process, which includes the following advantages: The process starts from readily available materials, avoids noxious reagents, is executed facilely and utilizes easily removable protecting groups.

The foregoing advantages and attributes render the peptides of this invention useful for the management of diabetes and the treatment of acromegaly.

SUMMARY OF THE INVENTION

The extended chain derivatives of this invention are represented for formulae 1 and 1a; formula 1 representing the cyclic peptides of this invention and formula 1a representing the linear reduced form of the peptides:

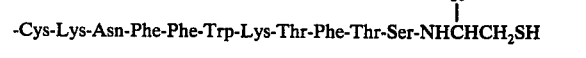

in which $R^1$ is H-, H-Gly- or H-Leu and $R^2$ is H or COOH.

The pharmaceutically acceptable salts of the compounds of formula 1 and 1a are included also within the scope of this invention.

The peptides of this invention are prepared by a process comprising:

reacting according to the azide coupling method a pentapeptide of formula

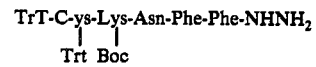

with a heptapeptide of formula

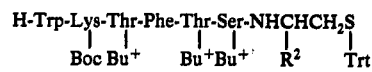

in which $R^2$ is hydrogen (H) or carboxyl (COOH) followed by removal of the terminal amino protecting group to obtain a peptide of formula

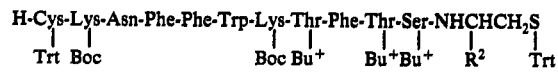

which is reacted with a peptide of formula $R^3$-Gly-Gly-Ala-Gly-NHNH$_2$ in which $R^3$ is Boc, Boc-Gly or Boc-Leu according to the azide coupling method to obtain a linear peptide of formula

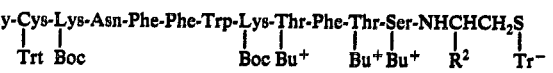

in which $R^2$ and $R^3$ are as defined herein; or alternatively, the latter linear peptide is also prepared by reacting according to the azide coupling method a peptide of formula $R^3$—Gly—Ala—Gly—NHNH$_2$ in which $R^3$ is as defined herein with a pentapeptide of formula

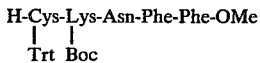

to obtain a peptide of formula

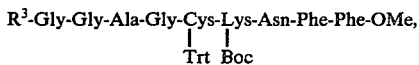

followed by hydrazinolysis of the latter compound to obtain a peptide of formula

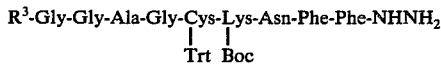

in which $R^3$ is as defined herein. Said last-named compound is reacted with a peptide of formula

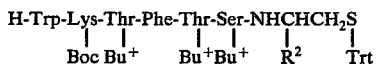

in which $R^2$ is as defined herein according to the azide coupling method to obtain a linear peptide of formula

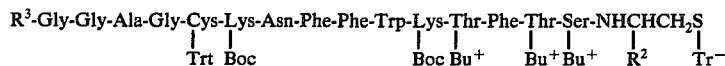

in which $R^2$ and $R^3$ are as defined herein; followed by oxidizing said last mentioned peptide, obtained by either method, with iodine or thiocyanogen to obtain the corresponding cyclic disulfide derivative of formula

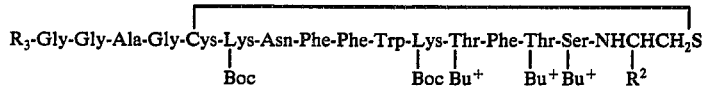

in which $R^2$ and $R^3$ are as defined herein and subsequently removing all remaining protecting groups under moderately acidic conditions to obtain the corresponding peptide of formula 1; or followed by subjecting said linear peptide to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative by treatment with hydrogen sulfide, oxidizing said last-named derivative by treatment with oxygen, 1,2-diiodoethane, sodium or potassium ferricyanide or iodine to obtain the corresponding cyclic disulfide derivative and removing the remaining protecting groups under moderately acidic conditions to obtain the desired peptide of formula 1. Alternatively, said cyclic disulfide derivative is reduced to said corresponding free disulfhydryl derivative by agents known to be effective for reducing known cyclic disulfides to their corresponding disulfhydryl derivatives.

A further aspect of this invention comprises the removal of all the protecting groups from the aforementioned linear peptide or the aforementioned disulfhydryl derivative under moderately acidic conditions to obtain the linear reduced form of the peptide of this invention of formula 1a,

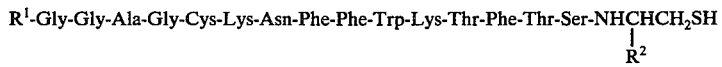

in which $R^1$ and $R^2$ are as defined herein.

The latter compound is also obtained by direct reduction of the cyclic peptides of formula 1 by agents known to be effective for reducing known cyclic disulfides to their corresponding disulfhydryl derivatives. If desired said reduced form of the cyclic peptide is converted to the corresponding peptide of formula 1 by one of the above oxidizing agents.

DETAILS OF THE INVENTION

In general the abbreviations used herein for designating the amino acids and the protective groups are based on recommendations of the IUPAC-IUB Commission on Biochemical Nomenclature, see Biochemistry, II, 1726–1732 (1972). For instance, Leu, Gly, Ala, Cys, Lys, Asn, Phe, Trp, Thr, and Ser represent the "residues" of L-leucine, glycine, alanine, L-cysteine, L-lysine, L-aspargine, L-phenylalanine, L-tryptophane, L-threonine and L-serine, respectively. By the residue is meant a radical derived from the corresponding L-amino acid by eliminating the OH portion of the carboxyl group and the H portion of the amino group. All the amino acids have the natural L-configuration.

A number of procedures or techniques for the preparation of peptides have hitherto been well established. For instance, the functional groups which are not involved in the peptide bond formation reaction are optionally protected by a protecting group or groups prior to the condensation reaction. For example, protecting groups which may be chosen for an amino function of a peptide or amino acid not involved in the peptide bond formation are: the alkoxycarbonyls which include benzyloxycarbonyl (represented by Z), t-butyloxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, ethoxycarbonyl, etc.; the acyl type protecting groups which include formyl, trifluoroacetyl, phthalyl, acetyl, toluenesulfonyl, etc.; the alkyl type protecting groups which include triphenylmethyl or trityl (represented by Trt), benzyl, etc. The preferred protecting groups ae benzyloxycarbonyl, t-butyloxycarbonyl, triphenylmethyl and α,α-dimethyl-3,5-dimethoxy-benzyloxycarbonyl. The protecting groups for the hydroxyl of serine and tyrosine are represented by acetyl, tosyl, benzoyl, tert-butyl (represented by $Bu^+$), trityl, and benzyl. The preferred protecting group is tert-butyl. The protecting group on the sulfur of cysteine or modified cysteine is illustrated by benzyl, triphenylmethyl or trityl (represented by Trt), benzyloxycarbonyl, acetamidomethyl (represented by Acm), etc.; the preferred protecting groups are trityl and acetamidomethyl. The carboxylic acid function of a peptide or amino acid can be considered protected by a lower alkyl or lower aralkyl ester which includes methyl (represented by OMe), ethyl (represented by OEt), benzyl (represented by OBzl), etc., and also by substituted hydrazides which includes t-butyloxycarbonyl hydrazide (represented by NHNH Boc), benzyloxycarbonyl hydrazides (represented by NHNH Z), α,α-dimethyl-3,5-dimethoxybenzyloxycarbonyl hydrazide (represented by NHNH Ddz), etc.

To promote facile condensation of the peptide carboxyl group with a free amino group of another peptide to form a new peptide bond, the terminal carboxyl group must be activated. Descriptions of these carboxyl-activating groups are found in general textbooks of peptide chemistry; for example K. D. Kopple, "Peptides and Amino Acids," W. A. Benjamin, Inc., New York, 1966, pp. 45 – 51 and E. Schröder and K. Lübke, "The Peptides;" Vol. 1, Academic Press, New York, 1965, pp. 77 – 128. Examples of the activated form of the terminal carboxyl are acid chloride, anhydride, azide, activated ester, o-acyl urea of a dialkylcarbodiimide, etc. The following activated esters have proved to be particularly suitable in the process of this invention; 2,4,5-trichlorophenyl (represented by OTcp), pentachlorophenyl (represented by OPcp), p-nitrophenyl (represented by ONp), succinimido and 1-benzotriazolyl.

The term "azide method" as used herein refers to the method of coupling two peptide fragments which comprises the reaction of a peptide hydrazide with a reagent which furnishes nitrous acid in situ. Suitable reagents for this purpose include an organic nitrite (e.g. t-butyl nitrite, isoamyl nitrite) or an alkali metal nitrite salt (e.g. sodium nitrite, potassium nitrite) in the presence of a strong acid such as hydrogen chloride or sulfuric or phosphoric acid. The corresponding peptide azide thus obtained is then reacted with a peptide having a free amino group to obtain the desired peptide. Preferred conditions for the azide method of coupling comprises reacting the peptide hydrazide with nitrous acid, generated in situ from an organic nitrite in the presence of a mineral acid, preferably hydrogen chloride, (pH ranging usually from 0.1 to 2), in an anhydrous inert organic solvent, for example, dimethyllformamide, dimethyl sulfoxide, ethyl acetate, methylene dichloride, tetrahydrofuran, dioxane, and the like at −30° to 20° C, preferably at about −15° C, for 10 to 30 minutes to obtain the corresponding azide. The peptide azide can be isolated and crystallized or preferably allowed to remain in the reaction medium, and thereafter reacting the azide in the said mixture with the peptide unit having the free amino group at temperatures ranging from −30° to 20° C for about one to two hours and then at 0° to 30° C for 10 to 30 hours. An acid acceptor, preferably an organic base, for example N-ethyldiisopropylamine, N-ethylmorpholine or triethylamine, is present in the reaction medium in order to make the reaction medium slightly alkaline, preferably pH 7.0 to 7.5. See also the above cited textbooks of Kopple and Schroder and Lubke for additional descriptions of this method.

The terms "peptide, polypeptide, tripeptide, hexapeptide, and the like" as used herein are not limited to refer to the respective parent peptides but also are used in reference to modified peptides having functionalized or protecting groups. The term "peptide" as used herein is used in reference to a peptide with one to seventeen amino acid residues. In addition the residue

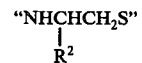

as used herein is used with reference to the residue of cysteine when $R^2$ is COOH, or to a modified residue of cysteine when $R^2$ is H.

The abbreviation Me represents a methyl group and $NHNH_2$ represents a hydrazide group.

The term "lower alkyl" as used herein contemplates hydrocarbon radicals having one to three carbon atoms and includes methyl, ethyl and propyl.

The term "mineral acid" as used herein contemplates the strong inorganic acids and includes hydrochloric, hydrobromic, sulfuric, phosphoric and the like. When the term is used in conjunction with an anhydrous system, hydrogen chloride is the preferred mineral acid.

The term "mildly acidic conditions" as used herein contemplates conditions in which a dilute aqueous solution of an organic acid, for example 30 – 80% aqueous formic, acetic or propionic acid, preferably 70 – 80%, or mixtures thereof, is a principal component of the reaction medium.

The term "moderately acidic conditions" as used herein contemplates conditions in which concentrated organic acids or solutions of the mineral acids are used as a principal component of the reaction medium at temperature ranging from about −30° to 30° C. Examples of preferred conditions in this case include the use of 50 to 100% trifluoroacetic acid at 0° to 30° C or 0.1 − 12N hydrochloric acid in aqueous or anhydrous organic solvents at −20° − 10° C.

The term "organic nitrite" includes the commercially availabe alkyl nitrites, for instance, t-butyl nitrite, isoamyl nitrite, and the like.

The term "organic base" as used herein includes triethylamine, N-ethylmorpholine, N-methylpiperidine, pyridine, N-ethyldiisopropylamine and the like.

The term "strong base" as used herein contemplates both organic bases, as described above, and strong inorganic bases including the hydroxides and carbonates of sodium and potassium.

The peptides of this invention, including the cyclic and the linear reduced forms, are obtained in the form of the free base or an acid addition salt either directly from the process of this invention or by reacting the peptide with one or more equivalents of the appropriate acid. Examples of preferred salts are those with pharmaceutically acceptable organic acids, e.g. acetic, lactic, succinic, benzoic, salicylic, methanesulfonic or toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. It should be noted that the peptides have three basic nitrogens giving rise to addition salts with one to possibly three equivalents of acid. If desired a particular acid addition salt is converted into another acid addition salt, e.g., a salt with a non-toxic, pharmaceutically acceptable acid, by treatment with the appropriate ion exchange resin in the manner described by R. A. Boissonas, et al., Helv. Chim. Acta, 43, 1349 (1960). Suitable ion exchange resins are cellulose based cation exchangers, for example carboxymethylcellulose or chemically modified, cross-linked dextran cation exchangers, for example, those of the Sephadex C type, and strongly basic anion exchanger resins, for example those listed in J. P. Greenstein and M. Winitz "Chemistry of the Amino Acids," John Wiley and Sons, Inc., New York and London, 1961, Vol. 2, p. 1456.

The peptides of this invention of formula 1 and 1a when $R^2$ is COOH also form addition salts with suitable pharmaceutically acceptable inorganic and organic bases. In this case the cyclic or linear reduced peptide is transformed into the correspnding pharmaceutically acceptable salt by treatment of the peptide with the appropriate inorganic or organic base. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkyl-amines, the alkyl radicals of which contain up to 3 carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, such as mono-, di- and triethanolamine; alkylenediamines which contain up to 6 carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine.

The peptides produced by the process of this invention, as well as their corresponding pharmaceutically acceptable salts, are useful because they possess the pharmacological activity of the natural tetradecapeptide somatostatin. Their activity is demonstrated readily in pharmacological tests such as a modification [A. V. Schally, et al., Biochem. Biophys. Res. Commun., 52, 1314 (1973); J. Rivier, et al., C. R. Acad. Sci. Paris, Ser. D, 276, 2737 (1973)] of the in vitro method of M. Saffran and A. V. Schally, Can. J. Biochem. Physiol., 33, 405 (1955).

The activity of the peptides of formula 1 or 1a of this invention is demonstrated also in vivo in a modification of the pentobarbital-induced increase in plasma growth hormone level in the rat as described by Brazeau, et al., cited above. In this test the peptides of this invention show a level of activity which is greater than or of the same order as somatostatin.

The peptides of this invention are used in mammals for the treatment of aromegaly and other hypersecretory endocrine states and in the management of diabetics: see for example, P. Brazeau, et al., cited above. When the peptide or a salt thereof is employed for such treatment or management, it is administered systemically, preferably parenterally, in combination with Boc-Asn-Phe-Phe-OMe. pharmaceutically acceptable liquid or solid carrier. The peptides of formula 1 or 1a have a low order of toxicity. The proportion of the peptide or salt thereof is determined by its solubility in the given carrier, by the given carrier, or by the chosen route of administration. The peptide or a salt thereof is used in a sterile aqueous solution which may also contain other solutes such as buffers or preservatives, as well as sufficiently pharmaceutically acceptable salts or glucose to make the solution isotonic. The dosage will vary with the form of administration and with the particular species to e treated and is preferably kept at a level of from 5 mcg ot 300 mcg per kilogram body weight. However, a dosage level in the range of from about 1 mcg to about 50 mcg per kilogram body weight is most desirably employed in order to achieve effective results.

The peptides or a salt thereof may also be administered in one of the long acting, slow-release or depot dosage forms described below, preferably by intramuscular injection or by implanation. Such dosage forms are designed to release from about 0.1 mcg to about 50 mcg per kilogram body weight per day.

It is often desirable to administer the agent continuously over prolonged periods of time in long-acting, slow-release or depot dosage forms. Such dosage forms may either contain a pharmaceutically acceptable salt of the agent having a low degree of solubility in body fluids, for example one of those salts described below, or they may contain the agent in the form of a water-soluble salt together with a protective carrier which prevents rapid release. In the latter case, for example, the agent may be formulated with a non-antigenic partially hydrolyzed gelatin in the form of a a viscous liquid; or the agent may be absorbed on a pharmaceutically acceptable solid carrier, for example, zinc hydroxide, and may be administered in suspension in a pharmaceutically acceptable liquid vehicle; or the agent may be formulated in gels or suspensions with a protective non-antigenic hydrocolloid, for example sodium carboxymethylcellulose, polyvinylpyrrolidone, sodium alginate, gelatin, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton; Pennsylvania 1970. Long-acting, slow-release preparations of the agent produced according to the process of this invention may also be obtained by microencapsulation in a pharmaceutically acceptable coating, for example gelatine, polyvinyl alcohol or ethyl cellulose. Further examples of coating materials and of the processes used for microencapsulation are described by J. a. Herbig in 37 Encyclopedia of Chemical Technology," Vol. 13, 2nd Ed., Wiley, New York 1967, pp 436 – 456. Such formulations, as well as suspensions of salts of the agent which are only sparingly soluble in body fluids, for example salts with pamoic acid or tannic acid are designed to release from about 5.0 mcg to about 100 mcg of the active compound per kilogram body weight per day, and are preferably administered by intramuscular injection. Alternatively, some of the solid dosage forms listed above, for example certain sparingly water-soluble salts or dispersions in or adsorbates on solid carriers of salts of the agent, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

Process

The process of this invention will be illustrated now by the following embodiments in which specific peptides of formulae 1 and 1a are prepared.

The protected lower alkyl ester of alanyl-glycine, preferably Boc-Ala-Gly-OMe [described by H. U. Immer et al., Helv. Chim. Acta, 57, 730 (1974)] is dissolved in trifluoroacetic acid and the solution is kept at 0° to 10°0 C for about one hour followed by evaporation of the trifluoroacetic acid to give H-Ala-Gly-OMe in the form of its trifluoroacetic acid addition salt which may, if desired, be converted to and used in the form of the free base. Other cleaving reagents for the removal of the Boc protecting group include hydrogen bromide in acetic acid, alcoholic solutions of hydrogen chloride, etc. Said last-named compound is dissolved in an inert organic solvent, preferably dimethylformamide, and the resulting solution cooled to about 0° to 10° C. An excess, preferably 1.1 to 1.3 equivalents of an organic base, preferably N-ethylmorpholine, is added to the solution; the solution now has a pH of about 8. Substantially one equivalent of a protected activated ester of glycine, preferably Boc-Gly-OTcp [described by J. Pless and R. A. Boissonnas, Helv. Chim. Acta, 46, 1609 (1963)] is added and the reaction mixture is kept at about 0° to 20° C for about 2 days. The solvent is evaporated and the residue crystallized to give the protected lower alkyl ester of glycylalanyl-glycine, preferably Boc-Gly-Ala-OMe which one treatment with trifluoroacetic acid in the aforementioned manner yields the lower alkyl ester of the tripeptide glycyl-alanyl-glycine, preferably H-GlyAla-Gly-OMe, in the form of the trifluoroacetic acid addition salt which may, if desired, be converted to the form of the free base. The latter tripeptide is reacted with Boc-Gly-OTcp in the aforementioned manner to yield the protected lower alkyl ester of glycyl-glycyl-alanyl-glycine, preferably Boc-Gly-Gly-Ala-Gly-OMe, which on treatment with the trifluoroacetic acid in the aforementioned manner yields the lower alkyl ester of glycyl-glycyl-alanyl-glycine, preferably H-Gly-Gly-Ala-Gly-OMe, in the form of its trifluoroacetic acid addition salt, and which may again, if desired, be converted to the form of the free base. The latter tetrapeptide is reacted with a protected activated ester of glycine, preferably Boc-Gly-OTcp, in the aforementioned manner to yield the lower alkyl ester of glycyl-glycyl-glycyl-alanyl-glycine, preferably Boc-Gly-Gly-Gly-ALA-Gly-OMe.

The above mentioned deprotected tetrapeptide, H-Gly-Gly-ala-Gly-OMe, preferably as the trifluoroacetic acid addition salt, is reacted with a protected activated ester of leucine, preferably ±-butyloxycarbonyl-leucine 1-benzotriazolyl ester; by combining at about 0° to 15° C in an inert organic solvent, preferably dimethylformamide, the above deprotected tetrapeptide, substantially 1.5 to 2.0 equivalents of Boc-Leu-OH, substantially 1.5 to 2.0 equivalents of 1-hydroxybenzotriazole, substantially 1.5 to 2.5 equivalents of dicyclohexylcarbodiimide and an excess of an organic base, preferably N-ethylmorpholine, to bring the pH of the solution to about 8. The resulting mixture is kept at about 0° to 15° C for 20 to 30 hours. Removal of the precipitate, evaporation of the filtrate and crystallization gives the protected lower alkyl ester of leucyl-glycyl-glycyl-alanyl-glycine, preferaby Boc-Leu-Gly-Gly-Ala-Gly-OMe.

The above mentioned tetrapeptide of formula Boc-Gly-Gly-Ala-Gly-OMe and the pentapeptides of formula Boc-Gly-Gly-Gly-Ala-Gly-OMe and Boc-Leu-Gly-Ala-Gly-OMe will herein be referred to as $R^3$-Gly-Gly-Ala-Gly-Ome in which $R^3$ is Boc, Boc-Gly and Boc-Leu, respectively.

The latter compounds of formula $R^3$-Gly-Gly-Ala-Gly-OMe in which $R^3$ is as defined herein are readily transformed to the corresponding hydroazides by reaction with an excess (20 to 50 molar equivalents) of hydrazine hydrate. Preferred conditions include treating said latter esters in an inert organic solvent, for example, methanol, n-butanol or dimethylformamide, with 40 to 50 molar equivalents of hydrazine hydrate at 0° to 30° C for about two hours to about one day. Removal of the solvent and excess hydrazine hydrate gives the corresponding amino protected hydrazides of $R^3$-glycyl-glycyl-alanyl-glycine, preferably $R^3$-Gly-Gly-Ala-Gly-NHNH$_2$ in which $R^3$ is Boc, Boc-Gly or Boc-Leu.

(a) Compounds 1 and 1a ($R^1$ = H and $R^2$ = COOH)

The preparation of the peptides of formula 1 and 1a ($R^1$ = H and $R^2$ = COOH) is achieved readily in the following manner:

The aforementioned tetrapeptide of formula Boc-Gly-Gly-Ala-Gly-NHNH$_2$ and a pentapeptide of formula

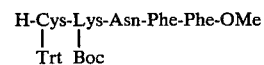

Phe-Phe-OMe (described by H.U. Immer et al., Helv. Chim. Acta, 57, 730 (1974) are coupled according to the azide coupling method to obtain the nonapeptide of formula

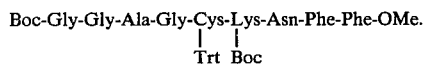

A convenient and efficacious procedure for this step comprises dissolving the peptide of formula Boc-Gly-Gly-Ala-Gly-NHNH$_2$ in an inert organic solvent, preferably dimethylformamide or a mixture of dimethylformamide and dimethyl sulfoxide. A solution of about two to five molar equivalents, preferably three molar equivalents, of a solution of a strong mineral acid in an organic solvent, preferably hydrogen chloride in ethyl acetate, is added to the latter solution at −20° to −10° C, preferably at about −15° C, and an organic nitrite, preferably ±-butyl nitrite, (1.0 to 1.5 molar equivalents, preferably 1.2 equivalents) is added to the stirred solution. After about 15 minutes at −20° to 0° C the mixture is rendered alkaline, preferably to about pH 7.0 – 7.5, with an excess of an organic base, preferably N-ethyldiisopropylamine, followed by the addition of substantially one equivalent of the above mentioned pentapeptide. A further addition of the organic base, preferably N-ethylmorpholine can be made to maintain the mixture slightly alkaline. The reaction mixture is then stirred at −10° to 0° C for 1 to 2 hours and then at 20° to 30° C for 20 to 30 hours. Evaporation or the solvent, taking up the residue in an organic solvent, preferably methanol, addition to a solvent in which precipitation occurs, preferably water or diethyl ether, and collection of the precipitate gives the aforementioned nonapeptide of formula

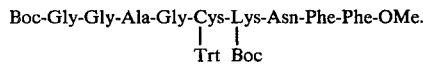

Briefly, the above requisite pentapeptide fragment described in the above publication is obtained readily by reaction an activated ester of Boc-Phe-OH with H-Phe-OMe, to obtain Boc-Phe-Phe-OMe, which after removal of the terminal protecting group (Boc) under moderately acidic conditions give H-Phe-Phe-OMe. In turn the latter compound is reacted with an activated ester of Boc-Asn-OH to obtain Boc-Asn-Phe-Phe-OMe. Subsequent removal of the terminal amino protecting group of the latter compound under moderately acidic conditions gives H-Asn-Phe-Phe-OMe.

Thereafter the latter compound is used to give the desired pentapeptide fragment by reacting the latter tripeptide with an activated ester

to obtain

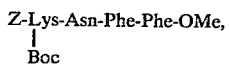

hydrogenating the last-named compound in the presence of a noble metal catalyst to obtain

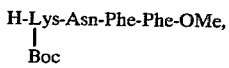

condensing the last-named compound with an activated ester of

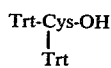

to obtain

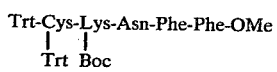

and removing the terminal N-protecting group (Trt) of said last-named compound under mildly acidic conditions to give the desired pentapeptide

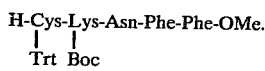

Returning now to the preparation of the compound of formulae 1 and 1a in which $R^1$ is H and $R^2$ is COOH, the aforementioned nonapeptide ester,

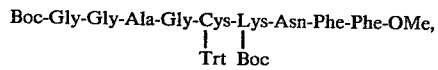

is transformed to the corresponding hydrazide by reaction with an excess of hydrazine hydrate in the same manner as described above to obtain the nonapeptide hydrazide of formula

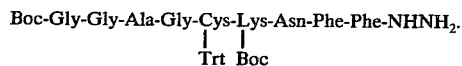

In the next step of the process of this invention said last-named compound and a heptapeptide of formula

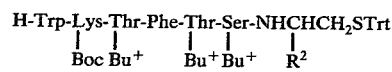

in which $R^2$ is COOH or alternatively written

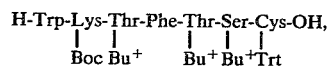

described by H.U. Immer et al., Helv. Chim. Acta, 57,730 (1974), are coupled according to the azide coupling method, described herein, to obtain the linear hexadecapeptide of formula

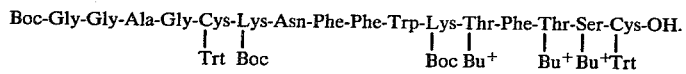

A convenient and efficacious procedure for this step comprises dissolving the first heptapeptide hydrazide in dimethylformamide. A solution of about two to five molar equivalents, preferably three molar equivalents, of a solution of a strong mineral acid in an organic solvent, preferably hydrogen chloride in ethyl acetate, is added to the latter solution at −20° to −10° C, preferably at about −15° C, and t-butyl nitrite (1.0 to 1.5 molar equivalents, preferably 1.2 equivalents) is added to the stirred solution. After about 15 minutes at −20° to 10° C a solution of substantially one equivalent of the heptapeptide and an organic base, preferably three to five equivalents of N-ethyldiisopropylamine in dimethylformamide cooled to about −15° C is added. The reaction mixture is then stirred at −20° to 0° C for 1 to 2 hours and then at 20° − 30° C for 15 to 25 hours. Evaporation of the solvent, trituration of the residue with water, methanol or a mixture of methanol and aqueous citric acid (2 to 2%) and separation of the solid gives the aforementioned linear hexadecapeptide which can be used without further purification for the subsequent step, see below.

The aforementioned requisite heptapeptide described in the above publication is obtained readily by reacting O-t-butylserine methyl ester with an activated ester of benzyloxycarbonyl-(O-t-butyl)-threonine to obtain

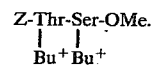

The terminal amino protecting group (Z) of the latter compounds is then removed by hydrogenation in the presence of a noble metal catalyst to afford

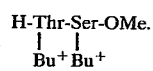

The latter methyl ester is then reacted with an activated ester of Z-Phe-OH to obtain

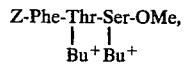

from which the terminal amino protecting group (Z) is removed subsequently by hydrogenation in the presence of a noble metal catalyst to give

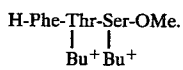

Next the latter tripeptide ester is reacted with an activated ester of

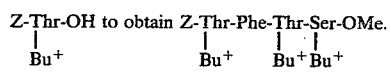

Again the terminal amino protecting group (Z) of the last-named compound is removed by hydrogenation in the presence of a noble metal catalyst to give

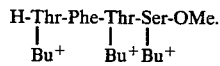

The latter compound is reacted with an activated ester of

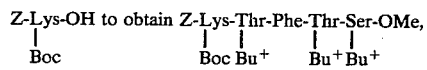

followed by removal of the terminal amino protecting group (Z) of the last-named compound by hydrogenation in the presence of a nobel metal catalyst to give

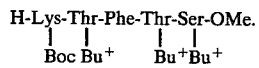

The latter compound is now reacted with an activated ester of Ddz-Trp-OH to obtain

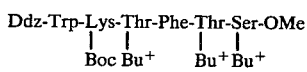

which in turn is reacted with hydrazine hydrate whereby the corresponding hexapeptide hydrazide,

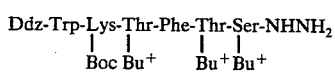

is isolated. This hexapeptide is now coupled with

according to the azide coupling method to give the corresponding heptapeptide,

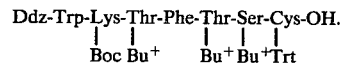

Treatment of the latter compound under mildly acidic conditions affords the desired heptapeptide in which $R^2$ is COOH.

The conversion of the preceding linear hexadecapeptide derivative in which $R^3$ is Boc and $R^2$ is COOH, obtained as described above, to the compound of formula I ($R^1$ = H and $R^2$ = COOH) is accomplished conveniently and efficiently by first subjecting the linear hexadecapeptide to the action of iodine, preferably in the presence of a lower alkanol or acetic acid, whereby concomitant removal of the sulfhydryl protecting groups, i.e. Trt, and formation of the disulfide bridge occurs to give the corresponding cyclic disulfide

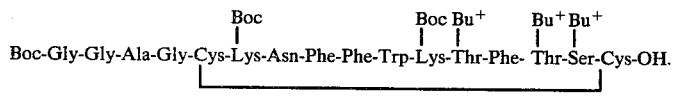

Subsequent treatment of the latter compound under moderately acidic conditions removes the remaining protecting groups (i.e. Boc and Bu+) to give the compound of formula I ($R^1$ = H and $R^2$ = COOH).

In a preferred embodiment of the above transformation the linear hexadecapeptide is dissolved in acetic acid or methanol, ethanol or other suitable lower alkanol, for example, propanol, isopropanol or butanol and the solution is added to an excess of iodine (5 to 25, preferably 10 molar equivalents) dissolved in one of the above solvents, preferably 2 – 5% iodine in methanol. The time and temperature of this reaction is not critical; however, it is desirable to keep the reaction between 0° and 30° C by regulating the addition of the iodine solution or by cooling of the reaction mixture, or by a combination of both. Under these conditions the addition usually takes 30 to 60 minutes. After the addition the mixture is stirred at 20° to 30° C for 30 to 120 minutes, preferably 60 minutes. Thereafter the mixture is cooled to about 0° C and an excess of a mild reducing agent, preferably sodium thiosulfate in aqueous solution is added. The mixture is concentrated and the residue is suspended in water. Collection of the solid material affords the desired corresponding cyclic disulfide derivative in the Boc and Bu+ protective groups are still present.

Alternatively, the linear hexadecapeptide can be converted to the aforementioned corresponding cyclic disulfide derivative by the method of R. G. Hiskey and R. L. Smith, J. Amer. Chem. Soc., 90, 2677 (1968) using thiocyanogen.

Again alternatively, the cyclic disulfide derivative is also obtained by selectively removing the sulfhydryl protecting groups of the above linear hexadecapeptide by the action of a mercuric or silver salt, for example nitrate, in an inert organic solvent, for example dimethylformamide or acetic acid, according to known methods; for example, see B. Kamber, and W. Rittel, Helv. Chem. Acta, 52, 1074 (1964), L. Zervas, et al., J. Amer. Chem. Soc. 87, 4922 (1965) and R. G. Denkewalter et al., J. Amer. Chem. Soc., 91, 502 (1969). The corresponding mercuric or disilver salt is then converted by hydrogen sulfide treatment to the corresponding free disulfhydryl derivative, see L. Zervas, et al., cited above. The latter derivative is then converted to the aforementioned cyclic disulfide derivative by a mild oxidizing agent selected from the group consisting of The linear reduced form of the hexadecapeptide (I; $R^1 =$ H and $R^2 =$ COOH) is obtained preferentially by removal of the protecting groups from the aforementioned linear hexadecapeptide of formula

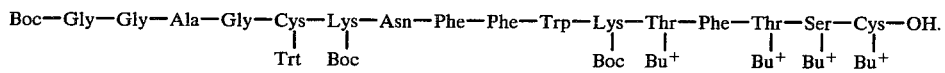

iodine according to the method described hereinbefore, oxygen according to the method of J. Rivier, et al., C. R. Acad. Sci. Ser. D, 276, 2737 (1973), 1,2-diiodoethane according to the method of F. Weygand and G. Zumach, Z. Naturforsch. 17b, 807 (1962), and sodium or potassium ferricyanide according to the method of D. Jarvis, et al., J. Amer. Chem. Soc., 83, 4780 (1961).

Finally, the aforementioned cyclic disulfide derivative is transformed into the hexadecapeptide of formula I ($R^1 =$ H and $R^2 =$ COOH) by subjecting the former to moderately acidic conditions whereby the remaining protecting groups of the cyclic disulfide derivative are removed. Generally this step is carried out by dissolving the cyclic disulfide derivative in an aqueous reaction medium containing a mineral acid at 0° to 20° C for 10 to about 60 minutes. Examples of such media are trifluoroacetic acid, 10 to 20% aqueous sulfuric acid, 10% phosphoric acid, 10 – 30% hydrobromic acid and 10 to 36% hydrochloric acid. An extremely useful medium is concentrated hydrochloric acid. Preferred conditions for the present step include dissolving the cyclic disulfide in a minium of concentrated hydrochloric acid cooled to 0° C and allowing the mixture to stir at 0° C for 5 to 10 minutes under a nitrogen atmosphere. Thereafter glacial acetic acid (10 X vols.) is added and the solution is cooled to about −70° C and lyophilized to give the cyclic hexadecapeptide. The latter product is purified further by ion exchange chromatography, preferably using a carboxymethyl cellulose cation exchanger and ammonium acetate as the eluant. In this case the product is obtained in the form of its acid addition salt with acetic acid. Alternatively, the product is purified by partition chromatography on a chemically modified cross-linked dextran, for example, Sephadex LH-20 or Sephadex G-25 using methanol or acetic acid, respectively, as the eluting solvent. In the case where Sephadex LH-20 and methanol as the eluting solvent is employed, the product is obtained in the form of its hydrochloric acid addition salt. In the case where Sephadex G-25 and acetic acid is employed, the product is obtained in the form of its acetic acid addition salt. Repeated lyophilization from water of the product in the form of its acetic acid addition salt yields a substantially pure hexadecapeptide of formula 1 ($R^1 =$ H and $R^2 =$ COOH) in the form of the free base, the cyclic disulfide of glycyl-glycyl-alanyl-glycyl-cysteinyl-lysyl-asparaginyl-phenyl-alanyl-phenylalanyl-tryptophyl-lysyl-threonyl-phenylalanyl-threonyl-phenylalanyl-threonyl-seryl-cysteine.

Convenient conditions for this deprotection step comprise dissolving the linear hexadecapeptide in concentrated hydrochloric acid at about 0° to 5° C in an inert atmosphere, for example, nitrogen or argon. The mixture is kept at this temperature for five to ten minutes. Subsequent isolation of the linear reduced form (Ia, $R^1 =$ H and $R^2 =$ COOH) is accomplished in the same manner as described previously for the isolation of the hexadepeptide derivative (I; $R^1 =$ H and $R^2 =$ COOH).

Also, the linear reduced form is obtained directly by reduction of the hexadecapeptide of formula I ($R^1 =$ H and $R^2 =$ COOH). Reduction with dithiothreitol according to the method of W. W. Cleland, Biochem. 3, 480 (1964) is preferred, although other agents known to be effective for the reduction of cyclic disulfides to the corresponding disulfhydryl derivative are applicable, for example, sodium bisulfite followed by hydrolysis of the intermediate dithiosulfate derivative.

(b) Compounds I and Ia ($R^1 =$ H-Leu and $R^2 =$ COOH)

The preparation of the peptides of formula I and Ia ($R^1 =$ H-Leu and $R^2 =$ COOH) are achieved readily in the following manner:

The aforementioned pentapeptide of formula Boc-Leu-Gly-Gly-Ala-Gly-NHNH$_2$ and the aforementioned pentapeptide of formula

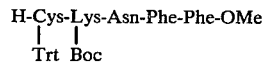

are coupled according to the azide coupling method in the same manner as described above to obtain the decapeptide of formula

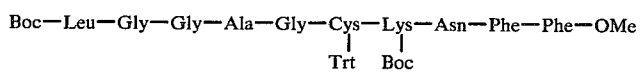

which is transformed to the corresponding hydrazide by reaction with an excess of hydrazine in the same manner as described above to obtain the decapeptide hydrazide of formula

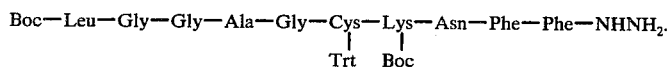

In the next step of the process of this invention said-last named compound and the above mentioned heptapeptide of formula

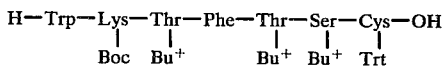

are coupled
according to the azide coupling method in the same manner as described for the preparation of the linear hexadecapeptide in (a) to obtain the linear heptadecapeptide of formula Boc-Leu-Gly-Gly-

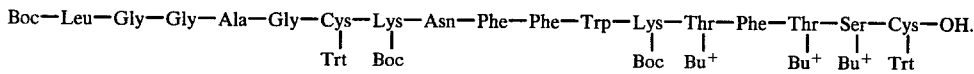

The conversion of the preceding linear heptadecapeptide to the compound of formula I ($R^1$ = H-Leu and $R^2$ = COOH) is accomplished conveniently and efficiently by first subjecting the last-mentioned linear heptadecapeptide to the action of iodine, preferably in the presence of methanol [as described previously for the preparation of the cyclic hexadecapeptide in (a)], whereby removal of the sulfhydryl protecting group, i.e. Trt, and formation of the disulfide bridge occurs to give the corresponding cyclic disulfide derivative of formula

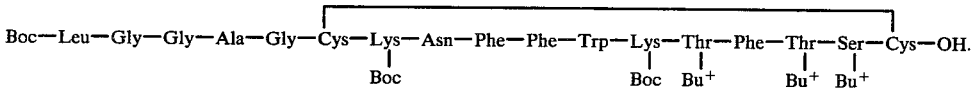

Subsequent treatment of the latter compound under moderately acidic conditions, preferably concentrated hydrochloric acid cooled to about 0° C [as described previously for the preparation of the cyclic hexadecapeptide in (a)], removes the remaining protecting groups (i.e., Boc and $Bu^+$) and further purification as described in (a) gives the heptadecapeptide of formula I ($R^1$=H-Leu and $R^2$=COOH) having the structure,

in the form of the free base or of an acid addition salt thereof.

The linear reduced form of the latter heptadecapeptide is obtained preferentially by removal of the protecting groups from the aforementioned linear heptadecapeptide of formula

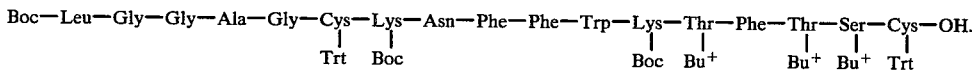

Convenient conditions for this deprotection step comprise dissolving the linear heptadecapeptide in concentrated hydrochloric acid in the manner previously described for the preparation of the linear reduced hexadecapeptide in (a). Alternatively, the linear reduced form is obtained by direct reduction of the above heptadecapeptide of formula I ($R^1$ = H-Leu and $R^2$ = COOH) in the manner described in (a).

(c) Compounds I and Ia ($R^1$ = H-Gly and $R^2$ = COOH)

The preparation of the peptides of formula I and Ia ($R^1$ = H-Gly and $R^2$ = COOH) are achieved readily in the following manner:

The protected lower alkyl ester of the pentapeptide cysteinyl-lysyl-asparaginyl-phenylalanyl-phenylalanine, preferably

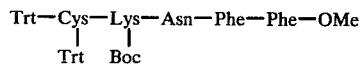

described above, is readily transformed to the corresponding hydrazide by reaction with an excess of hydrazine hydrate. Preferred conditions include treating the latter ester in an inert solvent, for example methanol, butanol, or dimethylformamide, with 20 to 40 molar equivalents of hydrazine hydrate at 0° to 30° C for one to two days. Removal of the solvent and crystallization gives the corresponding pentapeptide hydrazide of formula

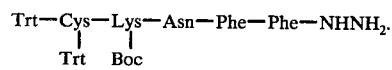

Said last-named compound and the heptapeptide of formula

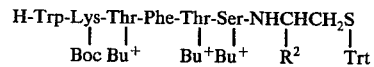

in which $R^2$ is COOH or alternatively written

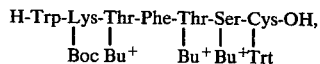

described above, are coupled according to the azide coupling method in the same manner as described above to obtain the dodecapeptide of formula

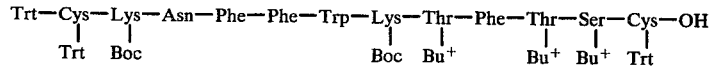

followed by removal of the terminal N-protecting group (Trt) of said last-named compound to obtain the dodecapeptide of formula

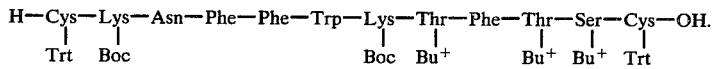

The removal of this protecting group (Trt) is accomplished readily under mildly acidic conditions. Preferred conditions include dissolving the dodecapeptide in a mixture of 5 to 15% formic acid in 60 to 80% acetic acid and allowing the solution to stand at 20° to 30° C for 3 to 10 hours. Concentration of the solution affords the dodecapeptide of formula

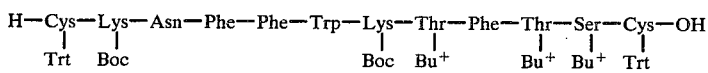

in the form of its formic acid addition salt which is, if desired, converted to the form of the free base.

Said last-named compound and a pentapeptide hydrazide of the formula Boc-Gly-Gly-Gly-Ala-Gly-NHNH$_2$, described above, are coupled according to the azide coupling method in the same manner as described above to obtain the linear heptadecapeptide of formula

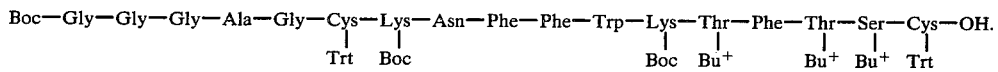

The conversion of the preceding linear heptadecapeptide to the compound of formula I ($R^1$ = H-Gly and $R^2$ = COOH) is accomplished conveniently and efficiently by first subjecting the last-mentioned linear heptadecapeptide to the action of iodine, preferably in the presence of methanol [as described previously for the preparation of the cyclic hexadecapeptide in (a)], whereby removal of the sulfhydryl protecting group, i.e. Trt, and formation of the disulfide bridge occurs to give the corresponding cyclic disulfide derivative of formula

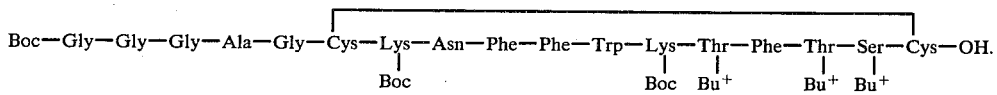

Subsequent treatment of the latter compound under moderately acidic conditions, preferably concentrated hydrochloric acid cooled to about 0° C [as described previously for the preparation of the cyclic hexadecapeptide in (a)], removes the remaining protecting groups (i.e., Boc and Bu$^+$) to give the heptadecapeptide of formula I ($R^1$ = H-Gly and $R^2$ = COOH) having the structure in the form of the free base or acid addition salt.

The linear reduced form of the latter heptadecapeptide is obtained preferentially by removal of the protecting groups from the aforementioned linear heptadecapeptide of formula

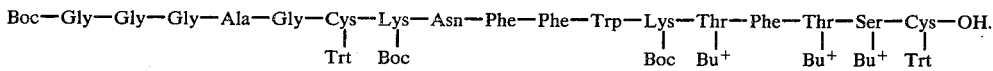

Convenient conditions for this deprotection step comprise dissolving the linear heptadecapeptide in concentrated hydrochloric acid in the manner previously described for the preparation of the linear reduced hexadecapeptide in (a). Alternatively, the linear reduced form is obtained by direct reduction of the above heptadecapeptide of formula I ($R^1$ = H-Gly and $R^2$ = COOH) in the manner described in (a).

(d) Compounds I and Ia ($R^1$ = H-Leu and $R^2$ = H)

The preparation of the peptides of formulae I and Ia ($R^1$ = H-Leu and $R^2$ = H) is achieved readily in the following manner:

The above pentapeptide hydrazide of formula

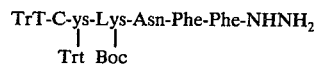

and a hexapeptide of formula

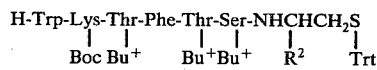

in which $R^2$ is H (described in the copending U.S. Pat. application Ser. No. 493,595; filed Aug. 1, 1974) are coupled according to the azide coupling method in the same manner, as described herein, to obtain the undecapeptide of formula

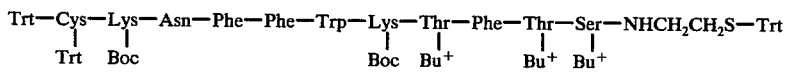

followed by removal of the terminal N-protecting group (Trt) of said last-named compound under mildly acidic conditions as described above in (c) to obtain the undecapeptide of formula

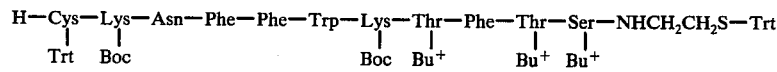

as the free base or preferably in the form of its formic acid addition salt.

Briefly the above requisite hexapeptide described in the above copending Patent Application, is obtained readily by coupling the above described hexapeptide hydrazide of formula

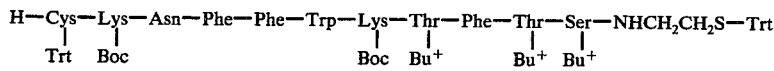

with 2-tritylthioethylamine according to the azide coupling method, described previously, to give the corresponding hexapeptide of formula

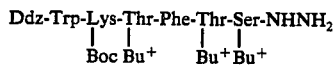

The latter compound under mildly acidic conditions gives the hexapeptide of formula

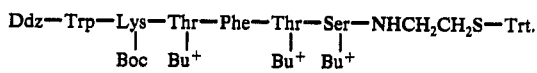

in the form of the formic acid addition salt which is, if desired, converted to the form of the free base.

The above described pentapeptide hydrazide of formula Boc-Leu-Gly-Gly-Ala-Gly-NHNH$_2$ is coupled with the above described undecapeptide of formula

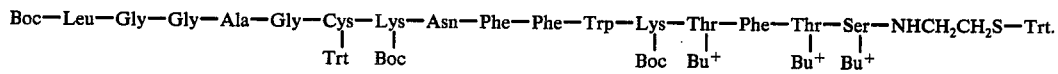

according to the azide coupling method, herein described, to obtain the linear hexadecapeptide of formula

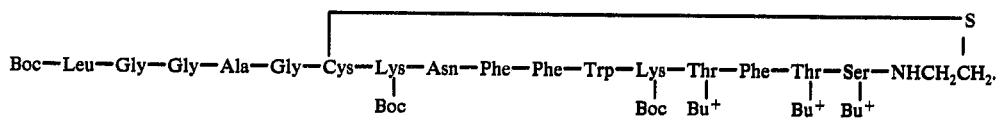

The conversion of the preceding linear hexadecapeptide to the compound of formula I ($R^1$ = H-Leu and $R^2$ = H) is accomplished conveniently and efficiently by first subjecting the last-mentioned linear hexadecapeptide to the action of iodine, preferably in the presence of methanol [as described previously for the preparation of the cyclic hexadecapeptide in (a)], whereby removal of the sulfhydryl protecting group, i.e. Trt, and formation of the disulfide bridge occurs to give the corresponding cyclic disulfide derivative of formula

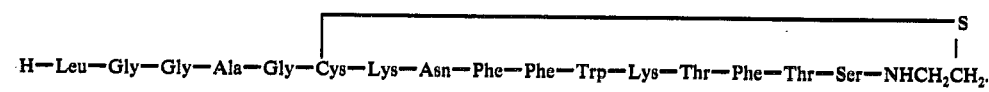

Subsequent treatment of the latter compound under moderately acidic conditions, preferably concentrated hydrochloric acid cooled to about 0° C [as described previously for the preparation of the cyclic hexadecapeptide in (a)], removes the remaining protecting groups (i.e., Boc and Bu$^+$), to give the hexadecapeptide of formula I ($R^1$ = H-Leu and $R^2$ = H) having the structure,

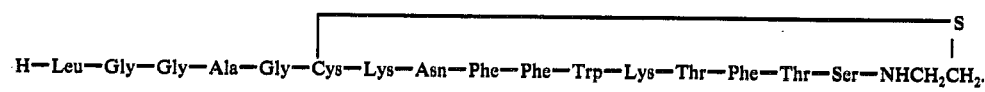

in the form of the free base or acid addition salt.

The linear reduced form of the latter hexadecapeptide is obtained preferentially by removal of the protecting groups from the aforementioned linear hexadecapeptide of formula

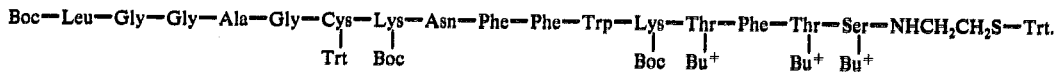

Convenient conditions for this deprotection step comprise dissolving the linear hexadecapeptide in concentrated step comprise dissolving the linear hexadecapeptide in concentrated hydrochloric acid in the manner previously described for the preparation of the linear reduced hexadecapeptide in (a). Alternatively, the linear reduced form is obtained by direct reduction of the above hexadecapeptide of formula I (R¹ = H-Leu and R² = H) in the manner described in (a).

(e) Compounds I and Ia (R¹ = H-Gly and R² = H)

The preparation of the peptides of formulae (R¹ = H-Gly and R² = H) are achieved readily in the following manner;

The above described pentapeptide hydrazide of formula Boc-Gly-Gly-Gly-Ala-Gly-NHNH₂ and the above described undecapeptide of formula

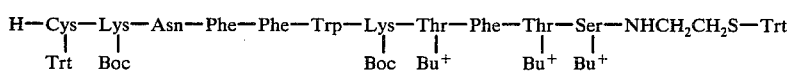

are coupled according to the azide coupling method herein described to obtain the hexadecapeptide of formula

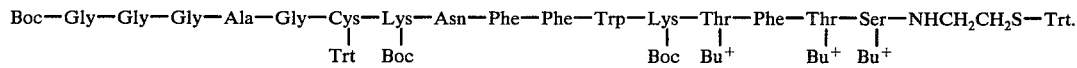

The conversion of the preceding linear hexadecapeptide to the compound of formula I (R¹ = H-Gly and R² = H) is accomplished conveniently and efficiently by first subjecting the last-mentioned linear hexadecapeptide to the action of iodine, preferably in the presence of methanol or acetic acid [as described previously for the preparation of the cyclic hexadecapeptide in (a)], whereby removal of the sulfhydryl protecting group, i.e. Trt, and formation of the disulfide bridge occurs to give the corresponding cyclic disulfide derivative of formula

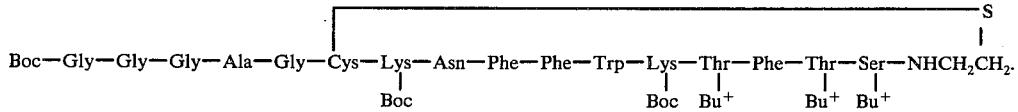

Subsequent treatment of the latter compound under moderately acidic conditions, preferably concentrated hydrochloric acid cooled to about 0° C [as described previously for the preparation of the cyclic hexadecapeptide in (a)], removes the remaining protecting groups (i.e., Boc and Bu⁺) to give the hexadecapeptide of formula I (R¹ = H-Gly and R² = H) have the structure,

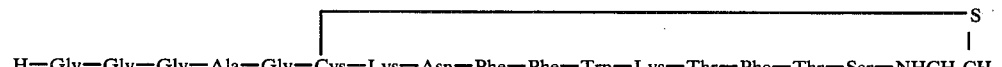

in the form of the free base or acid addition salt.

The linear reduced form of the latter heptadecapeptide is obtained preferentially by removal of the protecting groups from the aforementioned linear hexadecapeptide of formula

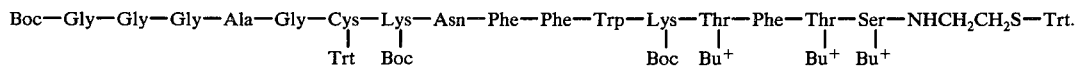

Convenient conditions for this deprotection step comprise dissolving the linear hexadecapeptide in concentrated hydrochloric acid in the manner previously described for the preparation of the linear reduced hexadecapeptide in (a). Alternatively, the linear reduced form is obtained by direct reduction of the above hexadecapeptide of formula I (R¹ = H-Gly and R² = H) in the manner described in (a).

(f) Compounds I and Ia (R¹ = H and R² = H)

The preparation of the peptides of formulae I and Ia (R¹ = H and R² = H) is achieved readily in the following manner:

The above described nonapeptide hydrazide of formula

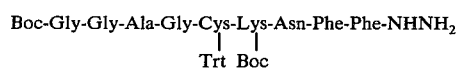

and the above described hexapeptide of formula

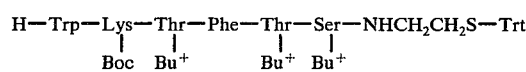

are coupled according to the azide coupling method herein described to obtain the pentadecapeptide of formula

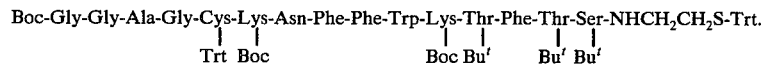

The conversion of the preceding linear pentadecapeptide to the compound of formula I (R¹ = H and R² = H) is accomplished conveniently and efficiently by first subjecting the last-mentioned linear pentadecapeptide to the action of iodine, preferably in the presence of methanol or acetic acid [as described previously for the preparation of the cyclic hexadecapeptide in (a)], whereby removal of the sulfhydryl protecting group, i.e. Trt, and formation of the disulfide bridge occurs to give the corresponding cyclic disulfide derivative of formula in the form of the free base or acid addition salt.

The linear reduced form of the latter pentadecapeptide is obtained preferentially by removal of the protecting groups from the aforementioned linear pentadecapeptide of formula

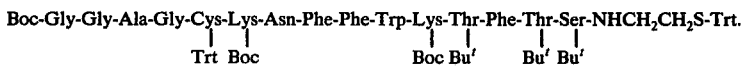

Convenient conditions for this deprotection step comprises dissolving the linear pentadecapeptide in concen-

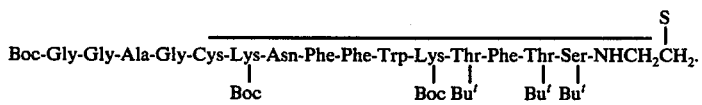

Subsequent treatment of the latter compound under moderately acidic conditions, preferably concentrated hydrochloric acid cooled to about 0° C [as described previously for the preparation of the cyclic hexadecapeptide in (a)], removes the remaining protecting groups (i.e., Boc and Bu+) to give the pentadecapeptide of formula I ($R^1 =$ H and $R^2 =$ H) having the structure trated hydrochloric acid in the manner previously described for the preparation of the linear reduced hexadecapeptide in (a). Alternatively, the linear reduced form is obtained by direct reduction of the above pentadecapeptide of formula I ($R^1 =$ H and $R^2 =$ H) in the manner described in (a).

The processes described above under (a) to (f) are represented by the following reaction diagrams:

H-Gly-Gly-Ala-Gly-Cys-Lys-Asn-Phe-Phe-Trp-Lys-Thr-Phe-Thr-Ser-NHCH$_2$CH$_2$—S

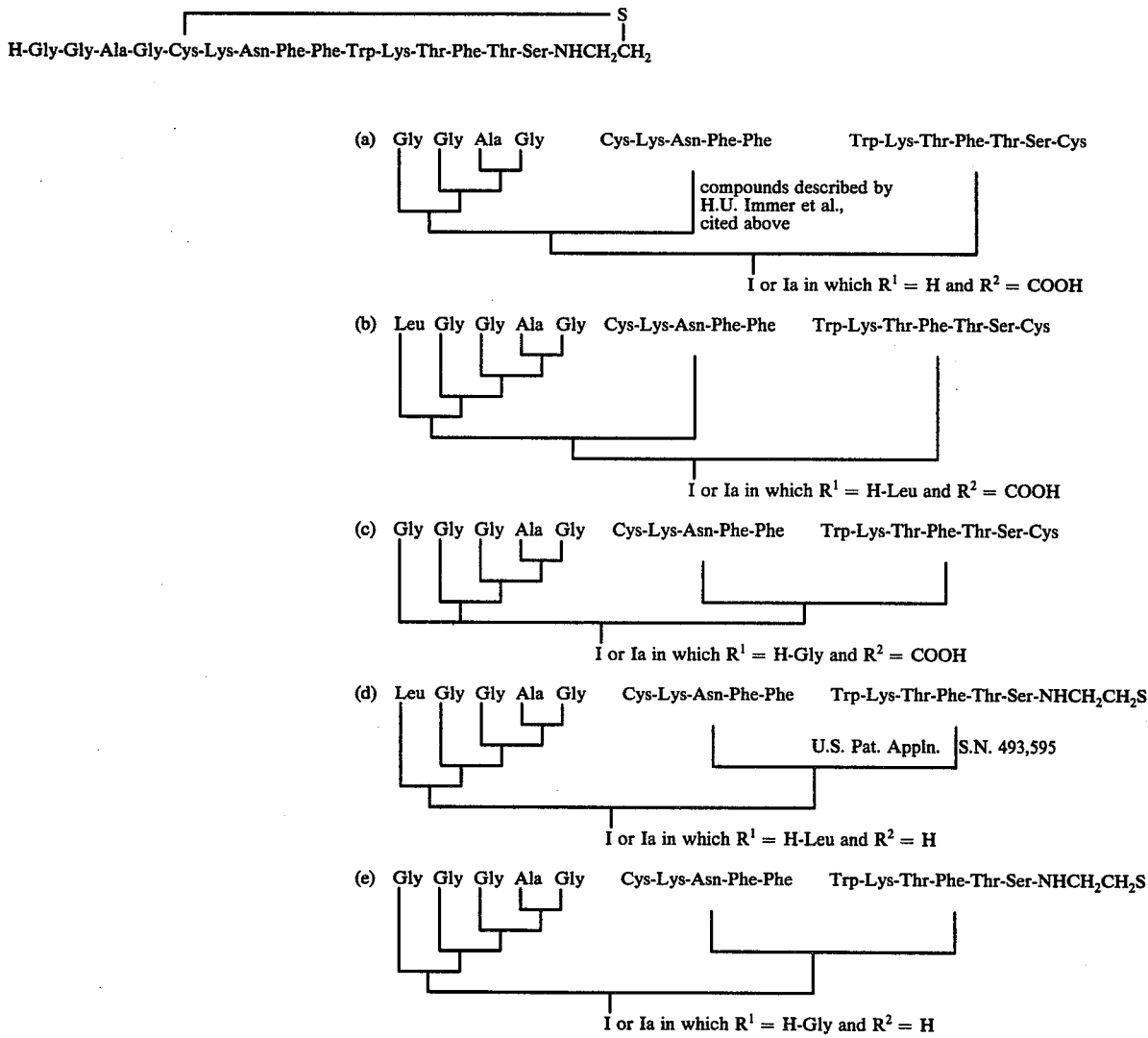

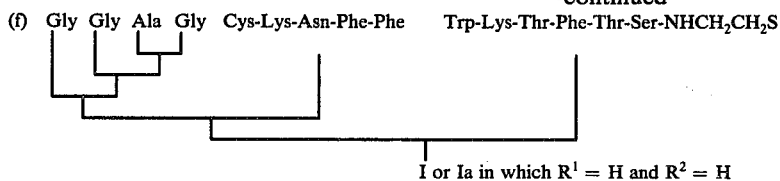

I or Ia in which $R^1 =$ H and $R^2 =$ H

Finally it will be apparent to those skilled in the art that: equivalent amino, hydroxy or thiol protecting groups, equivalent methods of coupling peptide fragments, and equivalent methods for removal of amino, hydroxy or thiol protecting groups, other than those disclosed herein can be used in the embodiments of this invention without departing from the scope and spirit of the invention. Such apparent alternatives are intended to be included within the scope of this invention.

The following flow diagram and examples illustrate further this invention.

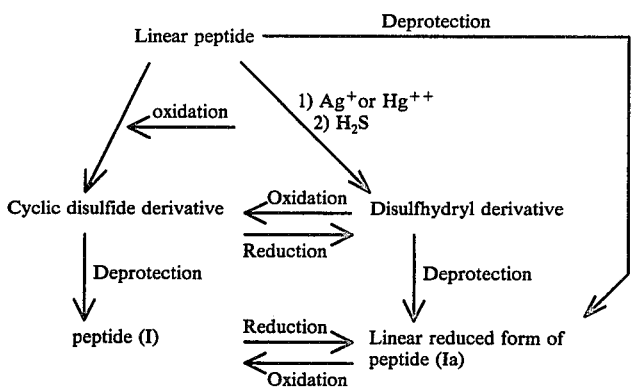

EXAMPLE 1

Alanyl-glycine Methyl Ester Trifluoroacetate (H-Ala-Gly-OMe.CF$_3$COOH)

Boc-Ala-Gly-OMe [10 g, 45 mmoles, described by H. U. Immer et al., Helv. Chim. Acta, 57, 730 (1974)] is dissolved in cold (ice bath) trifluoroacetic acid (100 ml). The solution is stirred for 1 hr at 0° C and the solvent evaporated. The residue is dissolved in methanol, added to diethyl ether and the precipitate collected to yield the title compound.

EXAMPLE 2 t-Butyloxycarbonyl-glycyl-alanyl-glycine Methyl Ester (Boc-Gly-Ala-Gly-OMe)

To H-Ala-Gly-OMe.CH$_3$CO$_2$H (45 mmoles, described in Example 1) in dimethylformamide (50 ml) is added N-ethylmorpholine (pH ~ 8) followed by a cold solution of Boc-Gly-OTcp (18 g, 45 mmoles) in dimethylformamide (50 ml). The solution is kept in an ice bath for 2 days. The solvent is evaporated and the product purified by column chromatography on silica gel using ethyl acetate-methanol-pyridine 98:1:1. The product is crystallized from ethyl acetate-petroleum ether to give the title compound; m.p. 98° – 100° C; nmr (DMSO-d$_6$); 1.25 δ (3H), 1.4 δ (9H), 3.68 δ (3H).

EXAMPLE 3

Glycyl-alanyl-glycine Methyl Ester Trifluoroacetate (H-Gly-Ala-Gly-OMe.CF$_3$COOH)

Boc-Gly-Ala-Gly-OMe (6.4 g, 20.1 mmoles, described in Example 2) is dissolved in cold (ice bath) trifluoroacetic acid (120 ml) and the solution stirred at 0° C for 1 hr. The solvent is evaporated, the residue dissolved in methanol and the product precipitated with the addition of diethyl ether. The precipitiate is collected to give the title compound.

EXAMPLE 4 t-Butyloxycarbonyl-glycyl-glycyl-alanyl-glycine Methyl Ester (Boc-Gly-Gly-Ala-Gly-OMe)

To a cold (ice bath), stirred solution of H-Gly-Ala-Gly-OMe.CH$_3$CO$_2$H (6.4 g, 20.03 mmoles, described in Example 3) in dimethylformamide (30 ml) is added N-ethylmorpholine (2.8 ml) followed by a solution of Boc-Gly-OTcp (8.5 g; 24 mmoles) in dimethylformamide (20 ml). The solution is kept in an ice bath for 2 days. The solvent is evaporated, the residue dissolved in methanol and the product precipitated with diethyl ether. Crystallization from ethyl acetate gives the title compound; mp 103° – 105° and 141° C (dimorphic); nmr 1.25 δ (3H), 1.38 δ (9H), 3.65 δ (3H).

EXAMPLE 5 t-Butyloxycarbonyl-glycyl-glycyl-alanyl-glycine Hydrazide (Boc-Gly-Gly-Ala-Gly-NH-NH$_2$)

To a cooled (ice bath), stirred solution of Boc-Gly-Gly-Ala-Gly-OMe (2.5 g, 6.7 mmoles, described in Example 4) in methanol (50 ml) is added hydrazine hydrate (2.5 ml). The solution is stirred at 0° C for 3 hr and at room temperature overnight. The precipitate is separated by filtration, washed with methanol and dried to yield the title compound; amino acid analysis: Gly 3, Ala 0.99.

EXAMPLE 6 t-Butyloxycarbonyl-glycyl-glycyl-alanyl-glycyl-S-trityl-cysteinyl-N$^\epsilon$-t-butyloxycarbonyl-lysyl-asparaginyl-phenylalanyl-phenylalanine Methyl Ester

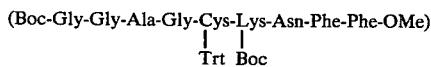

To a solution of Boc-Gly-Gly-Ala-Gly-NH-NH$_2$ (1.57 g, 4.2 mmoles, described in Example 5) in dimethyl sulfoxide (25 ml) and dimethylformamide (25 ml) is added a 2.04 N solution of hydrogen chloride in ethyl acetate (5.15 ml) at −10° C. The solution is cooled to −12° C and t-butyl nitrite (0.61 ml, 5.2 mmoles) is added. The solution is kept at −10° C for 15 min, cooled to −15° C and N-ethyldiisopropylamine (1.8 ml, pH 8) is added followed by a solution of

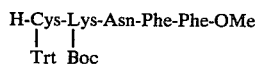

[4.5 g, 4.18 mmoles, described by H. U. Immer et al., Helv. Chim. Acta, 57, 730 (1974)] and N-ethyldiisopropylamine (0.72 ml) in dimethylformamide (25 ml). The mixture is stirred for 1 hr at −10° C and overnight at room temperature. After evaporation, the residue is dissolved in methanol, the product precipitated with water and crystallized from methanol to give the title compound; amino acid analysis: Lys, 1.07; Asp, 0.97; Gly, 3.27; Ala, 1.0; Phe, 2.08; Cysteic acid, 1.35.

EXAMPLE 7 t-Butyloxycarbonyl-glycyl-glycyl-alanyl-glycyl-S-trityl-cysteinyl-n$^\epsilon$-t-butyloxycarbonyl-lysyl-asparaginyl-phenylalanyl-phenylalanine Hydrazide

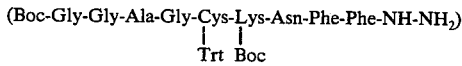

To a cold (ice bath) solution of

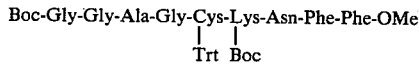

(0.9 g, 0.66 mmoles, described in Example 6) in dimethylformamide (25 ml) is added hydrazine hydrate (1.5 ml). The solution is stirred at room temperature for 18 hr. The solvent is evaporated, the residue triturated with methanol and dried over phosphorus pentoxide to give the title compound; amino acid analysis: Lys, 1.10; Asp, 1.00; Gly, 3.33; Ala, 1.0; Phe, 2.14; cysteic acid, 1.35.

EXAMPLE 8 t-Butyloxycarbonyl-glycyl-glycyl-alanyl-glycyl-S-trityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-S-trityl-cysteine

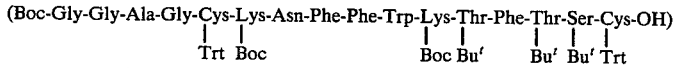

To a stirred solution at −20° C

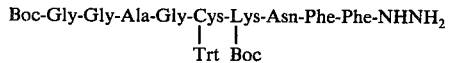

(800 mg, 0.59 mmole, described in Example 7) in dimethylformamide (12 ml) is added a 1.85 N solution of hydrogen chloride in ethyl acetate (0.795 ml, 1.475 mmole). The mixture is brought to −15° C, t-butyl nitrite (0.081 ml, 0.71 mmole) is added, and the solution is stirred for 15 min. A solution of

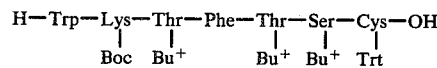

[816 mg, 0.59 mmole, described by H. U. Immer et al., Helv. Chim. Acta, 57, 730 (1974)] and N-ethyldiisopropylamine (0.354 ml, 2.06 mmole) in dimethylformamide (6 ml) is cooled to −15° C, and added to the above reaction mixture. The mixture is stirred at −15° C for 1 hr, and at 25° C for 18 hr. The solvent is evaporated, the residue triturated with ice cold citric acid, filtered, washed with water followed by methanol and dried to give the title compound; amino acid analysis: Lys, 1.94; Asp, 0.96; Thr, 1.64; Ser, 0.49; Gly, 2.82; Ala, 1.00; Phe, 2.80.

EXAMPLE 9

Cyclic Disulfide of glycyl-glycyl-alanyl-alanyl-glycyl-cysteinyl-lysyl-asparaginyl-phenylalanyl-phenylalanyl-tryptophyl-lysyl-threonyl-phenylalanyl-threonyl-seryl-cysteine (compound I, R$^1$ = H and R$^2$ = COOH)

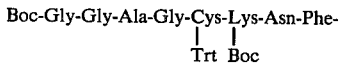

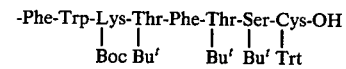

described in Ex. 8 (0.871 g, 0.32 mmole) is dissolved in glacial acetic acid (150 ml) and added dropwise at room temperature to a solution of iodine in methanol (0.5%, 150 ml, 30 mmoles) with stirring within 1 hr. The mixture is stirred for an additional 45 min, cooled in an ice bath and a solution of sodium thiosulfate in water (1N, 6ml) is added in order to destroy the excess of iodine (colorless solution). The solvent is evaporated and the residue triturated with water, dried and the dry product triturated with isopropyl ether to give the cyclic disulfide hexadecapeptide Boc-Gly-Gly-Ala-Gly- -continued

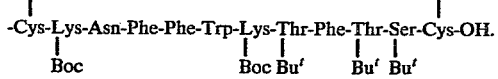

To the latter compound is added cold concentrated hydrochloric acid (23 ml) in an ice-water bath, under a nitrogen atmosphere with vigorous stirring. Stirring is continued for 10 min., glacial acetic acid (300 ml) is added and the solution is lyophilized. The residue is dissolved in water and again lyophilized. The residue is dissolved in 0.01 N aqueous ammonium acetate solution and applied to a column of carboxymethyl cellulose (Whatman CM-23, 2.5 × 30 cm). The pure compound is eluted with 0.06 N ammonium acetate buffer. The purified material is lyophilized from water to give the title compound as a white solid, in the form of its acetic addition salt; $\lambda_{max}^{MeOh}$ 282 nm ($\epsilon$ 5260), 289 nm ($\epsilon$4730), amino acid analysis: Lys, 2.28; Asp, 1.05; Thr, 1.95; Ser, 0.93; Cys, 2.34; Gly, 3.00; Ala, 1.05; Phe, 3.12. Repeated lyophilization of the latter product from water gives the title compound in the form of the free base; amino acid analysis: Lys, 2.10; Asp, 1.04; Thr, 1.80; Ser, 0.95; Cys, 2.17; Gly, 3.00; Ala, 1.07; Phe, 2.99.

In the same manner but using the thiocyanogen according to the method of Hiskey and Smith, cited above, instead of iodine, the title compound is also obtained.

EXAMPLE 10 t-Butyloxycarbonyl-leucyl-glycyl-glycyl-alanyl-glycine Methyl Ester (Boc-Leu-Gly-Gly-Ala-Gly-OMe)

A solution of Boc-Gly-Gly-Ala-Gly-OMe (2.0 g, 5.35 mmole, described in Example 4) in trifluoroacetic acid (25 ml) is stirred at 0° C for 1 hr. The solvent is evaporated, the residue triturated with ether, the solid collected and dried to give the tetrapeptide of formula H-Gly-Gly-Ala-Gly-OMe isolated as the trifluoroacetic acid addition salt.

A solution of the latter tetrapeptide (5.35 mmole), Boc-Leu-OH (2.31 g, 10 mmole), 1-hydroxybenzotriazole (1.35 g, 10 mmole), dicyclohexylcarbodiimide (2.27 g, 11 mole), and N-ethylmorpholine (0.68 ml) in dimethylformamide (25 ml) is stirred at 0° C for 24 hr. The mixture is filtered to remove the precipitate and the filtrate added to diethyl ether (200 ml). The precipitate is collected and crystallized from methanol-isopropyl ether to give the title compound: mp 190.5° - 193° C; $[\alpha]_D^{25} = -15.2°$ (c = 1, dimethylformamide).

EXAMPLE 11 t-Butyloxycarbonyl-leucyl-glycyl-glycyl-alanyl-glycine Hydrazide (Boc-Leu-Gly-Gly-Ala-Gly-NHNH$_2$)

A solution of Boc-Leu-Gly-Gly-Ala-Gly-OMe (2.0 g, 4 mmole, described in Example 10) and hydrazine hydrate (4.12 ml, 80 mmole) in methanol (50 ml) is stirred at 0° C for 4 hr. The solution is concentrated to 4 ml and added to diethyl ether (200 ml). The precipitate is collected, dissolved in methanol (4 ml) and added to diethyl ether (200 ml). The precipitate is collected and dried to give the title compound; mp 174° - 176.5° C; $[\alpha]_D^{24} = -12.0°$ (c = 1, dimethylformamide).

EXAMPLE 12 t-Butyloxycarbonyl-leucyl-glycyl-glycyl-alanyl-glycyl-S-trityl-cysteinyl N$^\epsilon$-t-butyloxycarbonyl-lysyl-asparaginyl-phenylalanyl-phenylalanine Methyl Ester

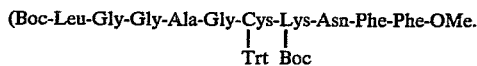

t-Butyl nitrite (0.15 ml, 1.27 mmole) is added to a solution of Boc-Leu-Gly-Gly-Ala-Gly-N$_2$H$_3$ (0.308 g, 0.635 mmole, described in Example 11) in dimethylformamide (5 ml) at $-20°$ C and 2.4 N hydrogen chloride in ethyl acetate (0.66 ml, 1.59 mmole). After stirring at $-20°$ C for 15 min, a solution of H-(Trt)Cys-(Boc)Lys-Asn-Phe-Phe-OMe[(0.62 g, 0.58 mmole, described by H. U. Immer et al. Helv. Chim. Acta., 57, 730 (1974)] and diisopropylethylamine (0.372 ml) in dimethylformamide (6 ml) is added. After stirring at $-20°$ C for 1 hr and at 0° for 24 hr, the solution is added to diethyl ether (200 ml). The precipitate is collected, dissolved in methanol (5 ml) and added to diethyl ether (200 ml). The precipitate is collected and dried to give the title compound, mp 238° - 240.5° C.

EXAMPLE 13 t-Butyloxycarbonyl-leucyl-glycyl-glycyl-alanyl-glycyl-S-trityl-cysteinyl-N$^\epsilon$-t-butyloxycarbonyl-lysyl-asparaginyl-phenylalanyl-phenylalanine Hydrazide

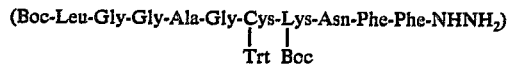

A solution of

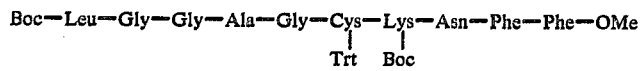

(0.56 g, 0.38 mmole, described in Example 12) and hydrazine hydrate (0.74 ml) in dimethylformamide (10 ml) is stirred at 0° C for 12 hr and at 25° C for 24 hr. The solution is added to diethyl ether (100 ml). The precipitate is collected, dissolved in dimethylformamide (3 ml), and added to diethyl ether (100 ml). The precipitate is collected and dried to give the title compound: mp 239° - 242° C; amino acid analysis: Lys, 1.05; Cysteic acid, 0.66; Asp, 0.99; Gly, 3.00; Ala, 1.11; 1/2 Cys, 0.21; Leu, 0.96; Phe, 1.86.

EXAMPLE 14 t-Butyloxycarbonyl-leucyl-glycyl-glycyl-alanyl-glycyl-S-trityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-S-trityl-cysteine

t-Butyl nitrite (0.03 ml, 0.28 mmole) is added to a solution at $-20°$ C of

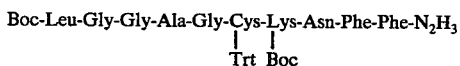

(0.20 g, 0.14 mmole described in Example 13) in dimethyl sulfoxide (2 ml), dimethylformamide (4 ml) and 2.21 N hydrogen chloride in ethyl acetate (0.16 ml, 0.35 mmole). After stirring at −20° C for 15 min, a solution of

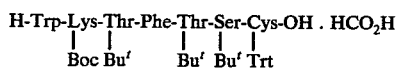

[0.20 g, 0.14 mmole, described by H. U. Immer et al., Helv. Chim. Acta, 57, 730 (1974)] and diisopropylethylamine (0.08 ml, 0.49 mmole) in dimethylformamide (5 ml) is added. The solution is stirred at −20° C for 1 hr and at 0° C for 24 hr. The solution is concentrated to 2 ml and added to diethyl ether (100 ml). The precipitate is collected, washed with water (2 × 5 ml), methanol (2 × 5 ml) and dried to give the title compound, amino acid analysis: Lys, 1.92; Cysteic acid, 0.93; Asp, 0.93; Thr, 1.38; Ser, 0.66; Gly, 3.00; Ala, 1.02; 1/2 Cys, 0.39; Leu, 0.93; Phe, 2.70.

EXAMPLE 15

Cyclic Disulfide of leucyl-glycyl-glycyl-alanyl-glycyl-cysteinyl-lysyl-asparaginyl-phenylalanyl-phenylalanyl-tryptophyl-lysyl-threonyl-phenylalanyl-threonyl-seryl-cysteine (compound 1, $R^1$ = H-Leu and $R^2$ = COOH)

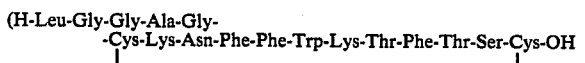

A solution of

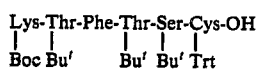

(0.23 g, 0.081 mmole described in Example 14) in acetic acid (90 ml) is added dropwise within 1 hr to a solution of 0.5% iodine in methanol (41.5 ml, 0.81 mmole). After completion of addition, the solution is stirred at room temperature for 1 hr and then cooled to 0° C. 1 N sodium thiosulfate (1.62 ml) is added until the solution becomes colorless. The solvent is collected, dried, triturated with ether and dried to give the cyclic disulfide heptadecapeptide of formula

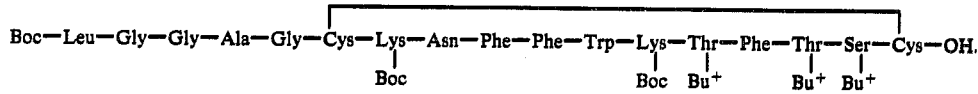

A solution of the cyclic disulfide heptadecapeptide (0.155 g, 0.066 mmoles) in concentrated hydrochloric acid (6.87 ml) under an atmosphere of nitrogen is rapidly stirred at 0° C for 8 min. Acetic acid (69 ml) is added and the solution lyophilized. The residue is lyophilized from water (50 ml). The residue is chromatographed on a column of a chemically modified cross-linked dextran "Sephadex G-25M" [3 × 50 cm, equilibrated in the lower phase and then equilibrated in the upper phase of n-butanol-acetic acid-water (4:1:5)] using the upper phase to desorb the peptide. The fractions containing the pure peptide are combined, evaporated, and lyophilized from water to give the title compound in the form of its acetic acid addition salt; $\lambda_{max}^{MeOH}$ 290 (ε 5000), 281 (ε 5540), 275 (ε 5205), 269 (ε 4980), 265 (ε 4625), 259 nm (ε 4085). Repeated lyophilization of the latter product from water gives the title compound in the form of the free base; amino acid analysis: Lys, 1.98; Cysteic acid, 1.41; Asp, 1.26; Thr, 1.92; Ser, 0.96; Gly, 3.00; Ala, 1.02; Leu, 0.96; Phe, 2.76.

In the same manner but using thiocyanogen according to the method of Hiskey and Smith, cited above, instead of iodine, the title compound is also obtained.

EXAMPLE 16 t-Butyloxycarbonyl-glycyl-glycyl-glycyl-alanyl-glycine Methyl Ester (Boc-Gly-Gly-Gly-Ala-Gly-OMe A solution of Boc-Gly-OTcp (3.7 g, 10.04 mmole), H-Gly-Gly-Ala-Gly-OMe.CF$_3$CO$_2$H (3.12 g, 8.03 mmole, described in Example 10), and N-ethylmorpholine (1.1 ml) in dimethylformamide (15 ml) is stirred at 0° C for 20 hr. The precipitate is collected and the filtrate added to diethyl ether. The two combined precipitates are crystallized from methanol to give the title compound: mp 198° – 201° C; $[α]_D^{24}$ = −3.9° (c=1, dimethylformamide).

EXAMPLE 17 t-Butyloxycarbonyl-glycyl-glycyl-glycyl-alanyl-glycine Hydrazide (Boc-Gly-Gly-Gly-Ala-Gly-NHNH$_2$)

A solution of Boc-Gly-Gly-Gly-Ala-Gly-OMe (1.0 g, 2.32 mmole, described in Example 16) and hydrazine hydrate (1 ml, 23.2 mmole) in methanol (30 ml) is stirred at 0° C for 4 hr. After evaporation the residue is triturated with diethyl ether and dried to give the title compound, mp 221° – 223° C.

EXAMPLE 18

N,S-Ditrityl-cysteinyl-N$^ε$-t-butyloxycarbonyl-lysyl-asparaginyl-phenylalanyl-phenylalanine Hydrazine

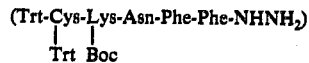

A solution of

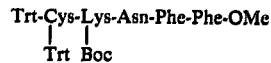

[1.25 g, 1.0 mmol, described by H. U. Immer et al., Helv. Chim. Acta, 57, 730 (1974)] and hydrazine hydrate (0.97 ml, 20 mmol) in methanol (30 ml) is stirred at 0° C for 2 days. The solvent is evaporated and the residue crystallized from ethanol-isopropyl ether to give the title compound, nmr (DMSO-d$_6$): δ 1.38 (s, 9H), 7.19–7.30 (m, 40H).

EXAMPLE 19

N,S-Ditrityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-S-trityl-cysteine

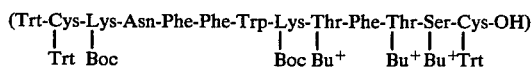

t-Butyl nitrite (0.09 ml, 0.74 mmole) is added to a solution at −20° C of

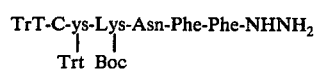

(0.62 g, 0.493 mmole, described in Example 18) in dimethylformamide (10 ml) and 2.6 N hydrogen chloride in ethyl acetate (0.475 ml, 1.23 mmole). After stirring at −20° C for 15 min, a solution of H-Trp-Lys-Thr-Phe-Thr-Ser-Cys-OH.HCOOH
          |   |      |   |   |
         Boc Bu$^+$   Bu$^+$ Bu$^+$Trt

[0.70 g, 0.493 mmole, described by H. U. Immer et al., Helv. Chim. Acta, 57, 730 (1974)] and diisopropylethylamine (0.30 ml, 1.65 mmole) in dimethylformamide (10 ml) is added. The solution is stirred at −20° C for 1 hr and at 25° C for 24 hr and evaporated. The residue is triturated with water, diethyl ether, cold 1 N citric acid and dried to give the title compound: nmr (CDCl$_3$) δ 1.08 and 1.13 (s, 27H), 1.37 (s, 18H), 7.28 (m, 60H); amino acid analysis: Lys, 2.23; Cysteic acid, 1.10; Asp, 1.00; Thr, 2.12; Ser, 1.02; 1/2 Cys, 0.64; Phe, 3.18.

EXAMPLE 20

S-Trityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-S-trityl-cysteine A solution of

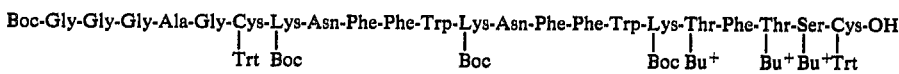

(0.50 g, 0.192 mmole, described in Example 19) in 6 ml of acetic acid-formic acid-water (7:1:2) is stirred at 25° C for 6 hr. The solvent is evaporated and the residue triturated with diethyl ether to give the title compound, amino acid analysis: Lys, 2.23; Cysteic acid, 1.38; Asp, 1.00; Thr, 2.14; Ser, 0.86; Phe, 3.24.

EXAMPLE 21 t-Butyloxycarbonyl-glycyl-glycyl-glycyl-alanyl-glycyl-S-trityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butylthreonyl-O-t-butyl-seryl-S-trityl-cysteine

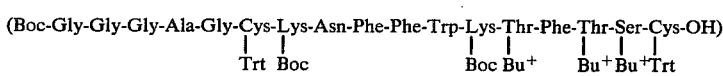

t-Butyl nitrite (0.04 ml, 0.34 mmole) is added to a solution at −20° of Boc-Gly-Gly-Ala-Gly-NHNH$_2$ (0.076 g, 0.176 mmole, described in Example 17) in dimethyl sulfoxide (1 ml), dimethylformamide (2 ml), and 2.5 N hydrogen chloride in ethyl acetate (0.176 ml, 0.44 mmole). After stirring at −20° C for 15 min, a solution of

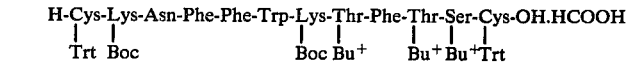

(0.385 g, 0.16 mmole, described in Example 20) and diisopropylethylamine (0.12 ml) in dimethylformamide (5 ml) is added. The solution is stirred at −20° C for 1 hr, at 0° C for 1 hr and at 25° C for 20 hr. The solvent is evaporated and the residue added to diethyl ether (100 ml). The precipitate is collected, washed with water, methanol and dried to give the title compound, amino acid analysis: Lys, 2.30; Cysteic acid, 1.42; Asp, 1.00; Thr, 2.27; Ser, 1.00; Gly, 3.84; Ala, 1.00; Phe, 3.34.

EXAMPLE 22

Cyclic disulfide of glycyl-glycyl-glycyl-alanyl-glycyl-cysteinyl-lysyl-asparaginyl-phenylalanyl-phenylalanyl-tryptophyl-lysyl-threonyl-phenylalanyl-threonyl-seryl-cysteine (compound 1, R$^1$ = H-Gly and R$^2$ = COOH)

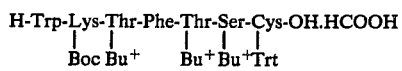

(0.285 g, 0.103 mmole, described in Example 21) in acetic acid (200 ml) is added to a solution of 0.5% iodine in methanol (52 ml, 1.03 mmole) over 60 min and allowed to stir for 60 min at room temperature. The solution is cooled to 0° C and 1 N sodium thiousulfate (2.06 mmole) is added in order to obtain a colorless solution. The solvent is evaporated and the oily residue added to

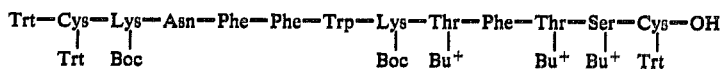

water (100 ml). The precipitate is collected and dried to give the cyclic disulfide heptadecapeptide of formula

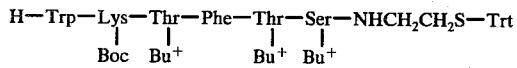

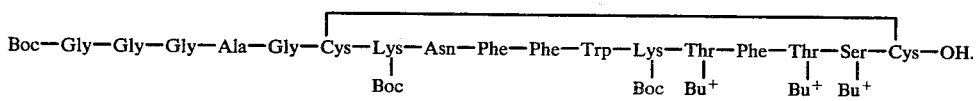

A solution of the last mentioned cyclic disulfide heptadecapeptide (0.10 mmole) in conc. hydrochloric acid (10 ml) is stirred at 0° C for 10 min under nitrogen. Acetic acid (100 ml) is added and the solution lyophilized. After another lyophilization from water (100 ml) the residue is subjected to partition chromatography on a column of a chemically modified cross-linked dextran ("Sephadex G-25M," 3 × 50 cm, made up in the lower phase of n-butanol-acetic acid-water (4:1:5) and then equilibrated in the upper phase) using the upper phase to desorb the substantially pure heptadecapeptide. The pure fractions are combined, evaporated, and lyophilized to give the title compound in the form of its acetic acid addition salt; $\lambda_{max}^{MeOH}$ 283 ($\epsilon$ 6702), 289 nm ($\epsilon$ 6350). Repeated lyophilization of the latter product from water gives the title compound in the form of a free base; amino acid analysis: Lys, 2.00; Cysteic acid, 1.42; Asp, 1.09; Thr, 1.89; Ser, 0.91; Gly, 3.64; Ala, 0.98; Phe, 295.

In the same manner but using thiocyanogen according to the method of Hiskey and Smith, cited above, instead of iodine, the title compound is also obtained.

EXAMPLE 23

N,S-Ditrityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butylseryl-2-tritylthioethylamide The pentapeptide hydrazide

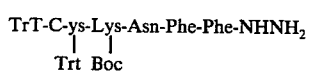

(0.80 g, 0.637 mmole, described in Example 18) is dissolved in dry dimethylformamide (9 ml) and cooled to −20° C. Hydrochloric acid in ethyl acetate (2.4 N, 0.691 ml) is added followed by t-butyl nitrite (0.0872 ml), 0.764 mmole). The mixture is stirred for 15 min at −15° C. A solution of (0.852 g, 0.637 mmole, prepared as described in the copending U.S. Patent Application Ser. No. 493,595; filed Aug. 1, 1974) in dimethylformamide (8 ml) containing N-ethyldiisopropylamine (0.272 ml, 1.59 mmole) is cooled to −15° C and added dropwise to the above reaction mixture. Stirring is continued at −15° C for 1 hr and at room temperature overnight. The reaction mixture is evaporated under reduced pressure, the residue triturated with water, filtered, washed with water and dried over phosphorous pentoxide. The residue is chromatographed on a column of silica gel (163 g) with chloroform containing methanol (3%) and pyridine (0.3%) as eluent and the pure product is crystallized from methanol-isopropyl ether to give the title compound: m.p. 163° − 180° C (dec.).

Analysis for $C_{149}H_{180}N_{16}O_{19}S_2$ Calc'd C, 69.85; H, 7.04; N, 8.75% Found C, 69.24; H, 7.09; N, 8.90%

EXAMPLE 24

S-Trityl-cysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonylphenylalanyl-O-t-butyl-theonyl-O-t-butyl-seryl-2-tritylthioethylamide Formate

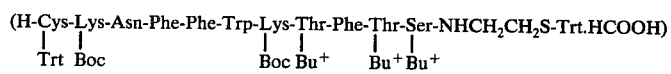

The undecapeptide

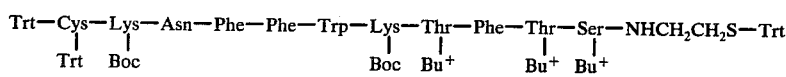

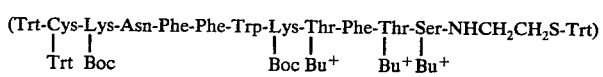

(0.909 g, 0.355 mmole, described in Example 23) is dissolved in acetic acid-formic acid-water mixture (7:12, 10 ml) and the solution is stirred overnight at room temperature. The solvent is evaporated and the residue triturated with water. The precipitate obtained is filtered, washed with water and dried over phosphorous pentoxide. The solid is triturated several times with petroleum ether/ether and dried to give the title compound, amino acid analysis: Lys, 2.03; Asp, 1.00; Ser, 0.87; Phe, 2.97; Cysteic acid, 0.90; Thr, 1.85.

EXAMPLE 25 t-Butyloxycarbonyl-leucyl-glycyl-glycyl-alanyl-glycyl-S-tritylcysteinyl-N$^\epsilon$-t-butyloxycarbonyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-2-tritylthioethylamide

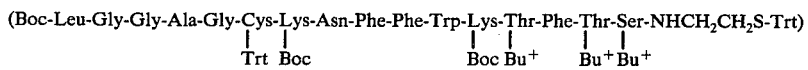

The pentapeptide hydrazide Boc-Leu-Gly-Gly-Ala-Gly-NHNH$_2$ (0.066 g, 0.136 mmole, described in Example 11) is dissolved in dry dimethylformamide (3 ml) and cooled to −20° C. Hydrochloric acid in ethyl acetate (2 N, 0.175 ml) is added, followed by t-butyl nitrite (0.0186 ml, 0.163 mmole). The mixture is stirred at −15° C for 15 min. A solution of

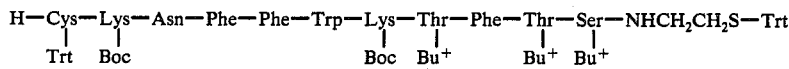

(0.315 g, 0.133 mmole, described in Example 24) in dimethylformamide (4ml) containing N-ethyldiisopropylamine (0.082 ml, 0.476 mmole) is cooled to −15° C and added dropwise to the above reaction mixture. Stirring is continued at −15° C for 1 hr and at room temperature overnight. The reaction mixture is evaporated under reduced pressure, the residue triturated with ice cold citric acid (1 N), filtered and washed with water. The solid residue is triturated with methanol and dried over phosphorus pentoxide to give the title compound; amino acid analysis: Lys, 1.88; Cysteic acid, 0.84; Asp, 1.00; Thr, 1.94; Ser, 0.97; Gly, 2.78; Ala, 0.89; Leu, 0.89; Phe, 3.11.

EXAMPLE 26

Cyclic disulfide of leucyl-glycyl-glycyl-alanyl-glycyl-cysteinyl-phenylalanyl-phenylalanyl-tryptophy-lysyl-threonyl-phenylalanyl-threonyl-seryl-2-thioethylamide (compound I, R$^1$ - H-Leu and R$^2$ = H)

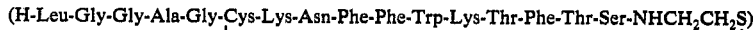

A solution of

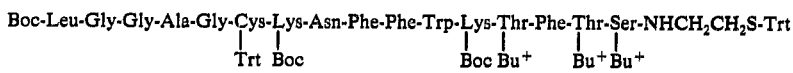

(0.230 g, 0.083 mmole, described in Example 25) in acetic acid (100 ml) is slowly added to a vigorously stirred solution of iodine (0.211 g, 0.83 mmole) in methanol (42 ml) at room temperature. After completion of addition, the solution is stirred at room temperature for 60 min. The solution is cooled to 0° C. and a solution of sodium thiosulfate in water (1 N) is slowly added to destroy the excess of iodine (colorless solution). The solvent is evaporated almost to dryness, the residue is triturated with cold water, filtered, washed with water, and dried over phosphorus pentoxide. The solid is washed with ether and dried to give the cyclic disulfide of formula

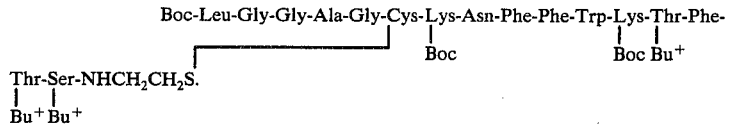

This cyclic hexadecapeptide is vigorously stirred at 0° C under an atmosphere of nitrogen for 10 min in conc. hydrochloric acid (7 ml). Acetic acid (90 ml) is added and the solution lyophilized. The residue is taken up in 2% acetic acid in water and lyophilized. The residue is subjected to partition chromatography on a column of a chemically modified cross-linked dextran ("Sephadex G-25M", 3 × 50 cm, equilibrated in the lower phase of n-butanol-acetic acid-water (4:1:5) and then equilibrated in the upper phase) using the upper phase to desorb the substantially pure hexadecapeptide. The pure fractions are combined, evaporated and lyophilized to give the title compound in the form of its acetic acid addition salt; $\lambda_{max}^{MeOH}$ 290 (4,290), 282 (4,910), 273 nm ($\epsilon$ 4,630). Repeated lyophilization of the latter product from water gives the title compound in the form of the free base; amino acid analysis: Lys, 2.01; Asp, 1.35; Ser, 0.93; Ala, 0.99; Phe, 2.52; Cysteic acid, 0.66; Thr, 1.98; Gly, 3.00; Leu, 0.96.

EXAMPLE 27 t-Butyloxycarbonyl-glycyl-glycyl-glycyl-alanyl-glycyl-S-trityl-cysteinyl-N$^\epsilon$-t-butyloxycarboyl-lysyl-asparaginyl-phenylalanyl-phenylalanyl-tryptophyl-N$^\epsilon$-t-butyloxycarbonyl-lysyl-O-t-butyl-threonyl-phenylalanyl-O-t-butyl-threonyl-O-t-butyl-seryl-2-tritylthioethylamide

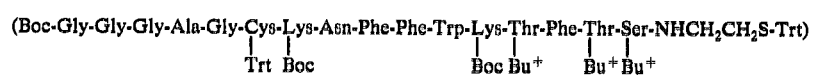

The pentapeptide hydrazide Boc-Gly-Gly-Gly-Ala-Gly-NHNH₂ (0.0608 g, 0.141 mmole, described in Example 17) is dissolved in dry dimethylformamide (6 ml) and dimethyl sulfoxide (2 ml) and cooled to −20° C. Hydrochloric acid in ethyl acetate (2N, 0.176 ml, 0.352 mmole) is added, followed by t-butyl nitrite (0.0194 ml. 0.169 mmole). The mixture is stirred at −15° C for 15 min. A solution of

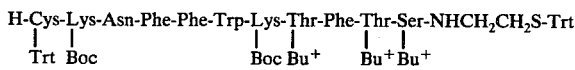

(0.327 g, 0.138 mmole, deacribed in Example 24) in dimethylformamide (4 ml) containing N-ethyldiisopropylamine (0.085 ml, 0.494 mmole) is cooled to −15° C and added dropwise to the above reaction mixture. Stirring is continued at −15° C for 1 hr and at room temperature overnight. The reaction mixture is evaporated under reduced pressure, the residue triturated with ice cold citric acid (1N), filtered and washed with water. The solid residue is triturated with methanol and dried over phosphorus pentoxide to give the title compound; amino acid analysis: Lys, 2.31; Cysteic acid, 0.84; Asp, 1.00; Thr, 2.26; Ser, 1.19; Gly, 4.00; Ala, 0.84; Phe, 3.2.

EXAMPLE 28

Cyclic disulfide of glycyl-glycyl-glycyl-alanyl-glycyl-cysteinyl-phenylalanyl-phenylalanyl-tryptophyl-lysyl-threonyl-phenylalanyl-threonyl-seryl-2-thioethylamide (compound 1, R¹ = H-Gly and R² = H)

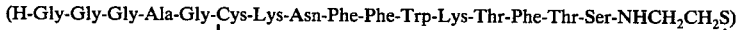

A solution of

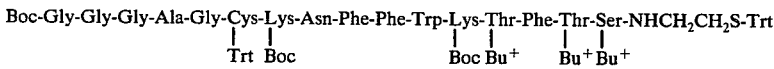

(0.224 g, 0.083 mmole, described in Example 27) in acetic acid (160 ml) is slowly added to a vigorously stirred solution of iodine (0.211 g, 0.83 mmole) in methanol (42 ml) at room temperature. After completion of addition, the solution is stirred at room temperature for 60 min. The solution is cooled to 0° C and a solution of sodium thiosulfate in water (1 N) is slowly added to destroy the excess of iodine (colorless solution). The solvent is evaporated almost to dryness, the residue is triturated with cold water, filtered, washed with water, and dried over phosphorus pentoxide. The solid is washed with ether and dried to give the cyclic disulfide of formula

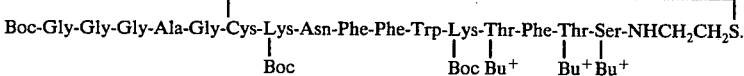

This cyclic hexadecapeptide is vigorously stirred at 0° C under an atmosphere of nitrogen for 10 min in conc. hydrochloric acid (7 ml). Acetic acid (90 ml) is added and the solution is lyophilized. The residue is taken up in 2% acetic acid in water and lyophilized. The residue is subjected to partition chromtography on a column of a chemically modified cross-linked dextran ("Sephadex G-25M," 3 × 50 cm, equilibrated in the lower phase of n-butanol-acetic acid-water (4:1:5) and then equilibrated in the upper phase) using the upper phase to desorb the substantially pure hexadecapeptide.

The pure fractions are combined, evaporated and lyophilized to give the title compound in the form of its acetic acid addition salt; $\lambda_{max}^{MeOH}$ 288 ($\epsilon$ 4870), 280 ($\epsilon$ 5575), 274 ($\epsilon$ 5380), 268 ($\epsilon$ 5185), 265 nm ($\epsilon$ 4955). Repeated lyophilization of the latter product from water gives the title compound in the form of a free base; amino acid analysis: Lys, 1.72; Asp, 1.00; Ser. 0.73; Ala, 0.69; Phe, 2.78; Cysteic acid, 0.57; Thr, 1.69; Gly, 3.59.

EXAMPLE 29 t-Butyloxycarbonyl-glycyl-glycyl-alanyl-glycyl-S-trityl-cysteinyl-N^ε-t-butyloxycarbonyl-lysyl-asparaginyl-phenylalanyl-phenylalanyl-tryptophyl-N^ε-t-butyloxycarbonyl-lysyl-O-t-butyl-threonyl-phenylalanyl-O-t-butyl-threonyl-O-t-butyl-seryl-2-tritylthioethylamide

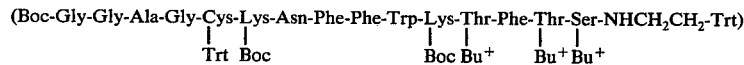

To a solution of

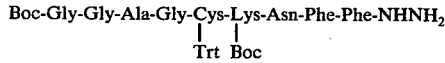

(800 mg, 0.59 mmole, prepared as described in Example 7) in dimethylformamide (12 ml) at −20° C there is added, with stirring, a 1.85 N solution of hydrogen chloride in ethyl acetate (0.795 ml. 1.475 mmole). The mixture is brought to −15° C, t-butyl nitrite (0.081 ml, 0.71 mmole) is added and the solution is stirred for 15 min. A solution of

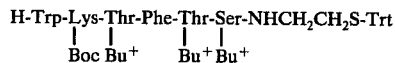

(0.852 g, 0.637 mmole, prepared as described in U.S. Pat. Appln. Ser. No. 493,595) and N-ethyldiisopropylamine (0.354 ml, 2.06 mmole) in dimethylformamide (6.0 ml) is cooled to −15° C and added to the above reaction mixture. The mixture is stirred at −15° C for 1 hr and at 25° C for 18 hr. The solvent is evaporated, the residue triturated with ice cold citric acid, filtered, washed with water followed by methanol and dried to give the title compound; amino acid analysis: Lys, 2.01; Asp, 0.97; Thr, 1.60; Ser, 0.65; Cysteic acid, 0.87; Gly, 2.92; Ala, 1.00; Phe, 2.97.

EXAMPLE 30

Cyclic Disulfide of glycyl-glycyl-alanyl-glycyl-cysteinyl-lysyl-asparaginyl-phenylalanyl-phenylalanyl-tryptophyl-lysyl-threonyl-phenylalanyl-threonyl-seryl-2-thioethylamide
(compound 1, $R^1 = H$ and $R^2 = H$)

(H-Gly-Gly-Ala-Gly-Cys-Lys-Asn-Phe-Phe-Trp-Lys-Thr-Phe-Thr-Ser-NHCH₂CH₂S)

Boc-Gly-Gly-Ala-Gly-Cys-Lys-Asn-Phe-Phe-Trp-Lys-Thr-Phe-Thr-Ser-NHCH₂CH₂S-Trt
                      Trt   Boc               Boc Bu⁺      Bu⁺ Bu⁺ described in Ex. 29 (0.860 g, 0.30 mmole) is dissolved in glacial acetic acid (150 ml) and added dropwise at room temperature to a solution of iodine in methanol (0.5%, 150 ml, 30 mmoles) with stirring within 1 hr. The mixture is stirred for an additional 45 min, cooled in an ice bath and a solution of sodium thiosulfate in water (1N, 6ml) is added in order to destroy the excess of iodine (colorless solution). The solvent is evaporated and the residue triturated with water, dried and the dry product triturated with isopropyl ether to give the cyclic disulfide pentadecapeptide Boc-Gly-Gly-Ala-Gly-Cys-Lys-Asn-Phe-Phe-Trp-Lys-Thr-Phe-Thr-Ser-NHCH₂CH₂S
                      Boc               Boc Bu⁺      Bu⁺ Bu⁺

To the latter compound is added cold concentrated hydrochloric acid (23 ml) in an ice-water bath, under a nitrogen atmosphere with vigorous stirring. Stirring is continued for 10 min., glacial acetic acid (300 ml) is added and the solution is lyophilized. The residue is dissolved in water and again lyophilized. The residue is dissolved in 0.01 N aqueous ammonium acetate solution and applied to a column of carboxymethyl cellulose (Whatman CM-23, 2.5 × 30 cm). The pure compound is eluted with 0.06 N ammonium acetate buffer. The purified material is lyophilized from water to give the title compound as a white solid, in the form of its acetic acid addition salt; $\lambda_{max}^{MeOH}$ 282 nm (ε 5120), 289 nm (ε 4610). Repeated lyophilization of the latter product from water gives the title compound in the form of the free base; amino acid analysis: Lys, 2.06, Asp, 1.02; Thr, 1.75; Ser, 0.91; Cysteic acid, 0.73; Gly, 3.00; Ala, 1.10; Phe, 3.11.

In the same manner but using thiocyanogen according to the method of Hiskey and Smith, cited above, instead of iodine, the title compound is also obtained.

We claim:

1. A process for preparing a peptide of formula I $R^1$-Gly-Gly-Ala-Gly-          (I)

in which $R^1$ is hydrogen, H-Gly or H-Leu and $R^2$ is hydrogen or carboxyl, which comprises: oxidizing a linear peptide of formula

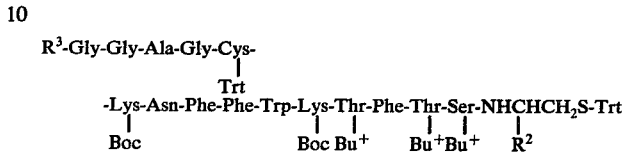

in which $R^3$ is Boc, Boc-Gly or Boc-Leu and $R^2$ is hydrogen or carboxyl with iodine or thiocyanogen to obtain the corresponding cyclic disulfide derivative of formula $R^3$-Gly-Gly-Ala-Gly-
      Boc            Boc Bu⁺   Bu⁺Bu⁺  $R^2$
    -Cys-Lys-Asn-Phe-Phe-Trp-Lys-Thr-Phe-Thr-Ser-NHCHCH₂S in which $R^2$ and $R^3$ are as defined herein and subsequently removing all remaining protecting groups under moderately acidic conditions to obtain the corresponding peptide of formula I; or followed by subjecting said linear peptide to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative by treatment with hydrogen sulfide, oxidizing said last-named disulfhydryl derivative by treatment with oxygen, 1,2-diiodoethane, sodium or potassium ferricyanide or iodine to obtain the corresponding cyclic disulfide derivative and removing the remaining protecting groups under moderately acidic conditions and isolating the desired peptide of formula I.

2. A process as claimed in claim 1 in which the linear peptide of formula

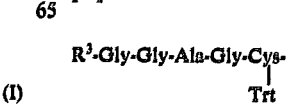

-continued

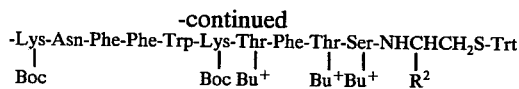

in which $R^2$ and $R^3$ are as defined therein is prepared by reacting according to the azide coupling method a pentapeptide of formula

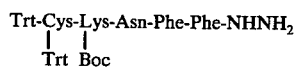

with a peptide of formula

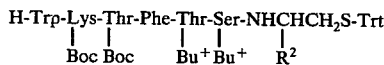

in which $R^2$ is as defined therein to obtain the corresponding peptide of formula

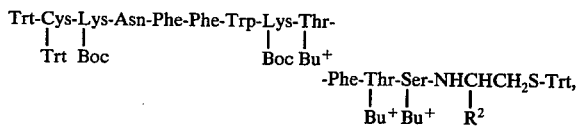

removing the terminal amino protecting group (Trt) of said last-named compound under mildly acidic conditions to obtain the corresponding peptide of formula

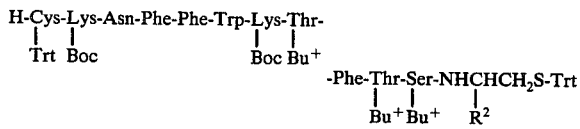

in which $R^2$ is as defined therein; followed by reacting said last-named compound with $R^3$-Gly-Gly-Als-Gly-NHNH$_2$ in which $R^3$ is as defined therein according to the azide coupling method and isolating said linear peptide.

3. A process as claimed in claim 1 in which the linear peptide of formula

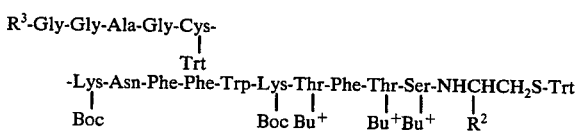

in which $R^2$ and $R^3$ are as defined therein is prepared by reacting according to the azide coupling method a peptide of formula $R^3$-Gly-Gly-Ala-Gly-NHNH$_2$ in which $R^3$ is as defined therein with a pentapeptide of formula

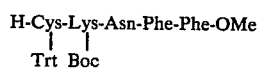

to obtain the corresponding peptide of formula

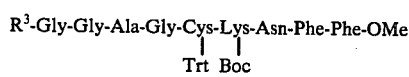

in which $R^3$ is as defined therein, followed by reacting said last-named compound with hydrazine hydrate to obtain the corresponding peptide of formula

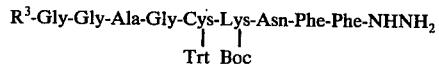

in which $R^3$ is as defined therein and reacting said last-named compound with a peptide of formula

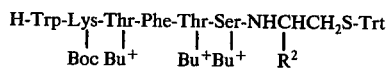

in which $R^2$ is as defined therein according to the azide coupling method and isolating said linear peptide,

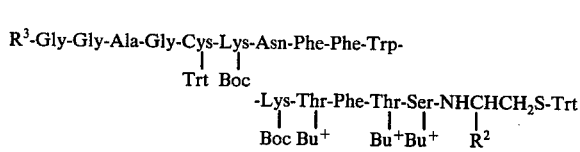

in which $R^2$ and $R^3$ are as defined therein.

4. The process as claimed in claim 1 wherein said linear peptide is subjected to treatment with iodine at from about 0° to 30° C for about 30 to 180 minutes in a lower alkanol or acetic acid to obtain the corresponding cyclic disulfide derivative.

5. A compound of the formula I or Ia

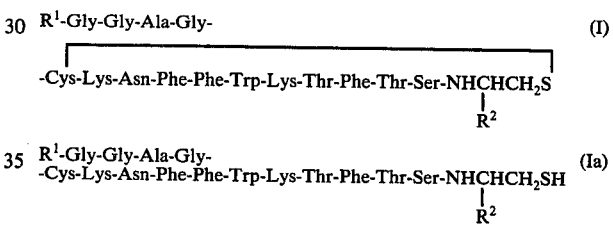

in which $R^1$ is hydrogen, H-Gly or H-Leu and $R^2$ is hydrogen or carboxyl.

6. The compound of claim 5 in which $R^1$ is hydrogen and $R^2$ is carboxyl.

7. The compound of claim 5 in which $R^1$ is H-Gly and $R^2$ is hydrogen.

8. The compound of claim 5 in which $R^1$ is H-Gly and $R^2$ is carboxyl.

9. The compound of claim 5 in which $R^1$ is H-Leu and $R^2$ is hydrogen.

10. The compound of claim 5 in which $R^1$ is H-Leu and $R^2$ is carboxyl.

11. The compound of claim 5 in which $R^1$ is hydrogen and $R^2$ is hydrogen.

12. A compound of formula

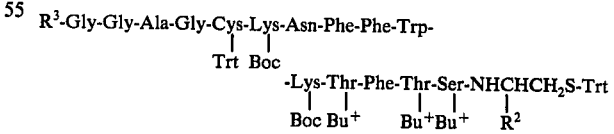

in which $R^2$ is hydrogen or carboxyl and $R^3$ is Boc, Boc-Gly or Boc-Leu.

13. The compound of claim 12 in which $R^2$ is carboxyl and $R^3$ is Boc.

14. The compound of claim 12 in which $R^2$ is hydrogen and $R^3$ is Boc-Gly.

15. The compound of claim 12 in which $R^2$ is carboxyl and $R^3$ is Boc-Gly.

16. The compound of claim 12 in which $R^2$ is hydrogen and $R^3$ is Boc-Leu.

17. The compound of claim 12 in which $R^2$ is carboxyl and $R^3$ is Boc-Leu.

18. The compound of claim 12 in which $R^2$ is hydrogen and $R^3$ is Boc.

19. A compound of the formula

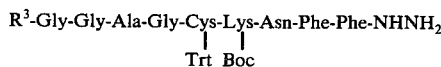

in which $R^3$, is Boc, Boc-Gly or Boc-Leu.

20. A pharmaceutically acceptable acid addition salt of the compound of formula I or Ia as claimed in claim 5.

21. The acid addition salt of claim 20 in which the acid is hydrochloric acid.

22. The acid addition salt of claim 20 in which the acid is acetic acid.

23. A method of treating acromegaly in a mammal which comprises administering to said mammal an effective dose of a compound of formula I or Ia as claimed in claim 5 or a pharmaceutically acceptable salt thereof together with a pharmaceutically acceptable carrier.

24. A pharmaceutical composition comprising a compound of formula I or Ia as claimed in claim 5 or a pharmaceutically acceptable salt thereof and pharmaceutically acceptable carrier.

25. A method of treating diabetes in a mammal which comprises administering to said mammal an effective dose of compound of formula I or Ia as claimed in claim 5 or a pharmaceutically acceptable salt thereof together with a pharmaceutically acceptable carrier.

26. A compound of formula

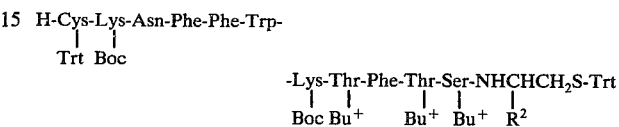

in which $R^2$ is hydrogen or carboxyl.

27. A compound of the formula $R^3$-Gly-Gly-Ala-Gly-NHNH$_2$ in which $R^3$ is Boc, Boc-Gly or Boc-Leu.

* * * * *